(12) United States Patent
Naka et al.

(10) Patent No.: US 9,611,475 B2
(45) Date of Patent: Apr. 4, 2017

(54) PROPHYLACTIC AND/OR THERAPEUTIC AGENT FOR INFLAMMATORY DISEASE, AND METHOD FOR SCREENING PROPHYLACTIC AND/OR THERAPEUTIC DRUG FOR INFLAMMATORY DISEASE

(71) Applicant: National Institutes of Biomedical Innovation, Health and Nutrition, Osaka (JP)

(72) Inventors: Tetsuji Naka, Osaka (JP); Minoru Fujimoto, Osaka (JP); Satoshi Serada, Osaka (JP)

(73) Assignee: National Institutes of Biomedical Innovation, Health and Nutrition, Osaka (JP)

( * ) Notice: Subject to any disclaimer, the term of this patent is extended or adjusted under 35 U.S.C. 154(b) by 0 days.

(21) Appl. No.: 14/783,713

(22) PCT Filed: Apr. 11, 2014

(86) PCT No.: PCT/JP2014/060552
§ 371 (c)(1),
(2) Date: Oct. 9, 2015

(87) PCT Pub. No.: WO2014/168247
PCT Pub. Date: Oct. 16, 2014

(65) Prior Publication Data
US 2016/0083725 A1  Mar. 24, 2016

(30) Foreign Application Priority Data
Apr. 11, 2013 (JP) ................................. 2013-083397

(51) Int. Cl.
| | | |
|---|---|---|
| A61K 31/70 | (2006.01) | |
| C12N 15/113 | (2010.01) | |
| A61K 31/7088 | (2006.01) | |
| A61K 31/7105 | (2006.01) | |
| A61K 31/711 | (2006.01) | |
| C07K 16/18 | (2006.01) | |
| G01N 33/50 | (2006.01) | |
| A61K 45/06 | (2006.01) | |
| A61K 49/00 | (2006.01) | |
| C12Q 1/68 | (2006.01) | |
| A01K 67/027 | (2006.01) | |
| C07H 21/02 | (2006.01) | |
| C07H 21/04 | (2006.01) | |

(52) U.S. Cl.
CPC ........ *C12N 15/113* (2013.01); *A01K 67/0276* (2013.01); *A61K 31/7088* (2013.01); *A61K 31/711* (2013.01); *A61K 31/7105* (2013.01); *A61K 45/06* (2013.01); *A61K 49/0008* (2013.01); *C07K 16/18* (2013.01); *C12Q 1/6883* (2013.01); *G01N 33/5023* (2013.01); *A01K 2207/20* (2013.01); *A01K 2217/075* (2013.01); *A01K 2227/105* (2013.01); *A01K 2267/0325* (2013.01); *A01K 2267/0368* (2013.01); *C07K 2317/76* (2013.01); *C12N 2310/11* (2013.01); *C12N 2310/12* (2013.01); *C12N 2310/14* (2013.01); *C12N 2320/30* (2013.01); *C12Q 2600/136* (2013.01); *C12Q 2600/158* (2013.01); *G01N 2333/4706* (2013.01); *G01N 2333/4728* (2013.01); *G01N 2500/04* (2013.01)

(58) Field of Classification Search
None
See application file for complete search history.

(56) References Cited

U.S. PATENT DOCUMENTS

| | | | |
|---|---|---|---|
| 8,790,647 B2 * | 7/2014 | Greenwood | ........... C07K 14/47 424/141.1 |
| 2011/0117111 A1 * | 5/2011 | Kwon | ................... C12N 15/111 424/172.1 |
| 2012/0034226 A1 | 2/2012 | Yoshida et al. | |
| 2012/0231002 A1 * | 9/2012 | Greenwood | ........... C07K 14/47 424/139.1 |

FOREIGN PATENT DOCUMENTS

| | | |
|---|---|---|
| JP | 2010-286279 A | 12/2010 |
| JP | 2011-83279 A | 4/2011 |
| JP | 2011-116697 A | 6/2011 |
| WO | 2009/120877 A2 | 10/2009 |

OTHER PUBLICATIONS

Nakajima, "New Biomarker for psoriasis: Leucine-rich alpha-2 glycoprotein," *The 27th Annual Meeting of the Japanese Society for Psoriasis Research*, Sep. 7, 2012, 4 pages.
Serada et al., "iTRAQ-based proteomic identification of leucine-rich α-2 glycoprotein as a novel inflammatory biomarker in autoimmune diseases," *Ann Rheum Dis* 69:770-774, 2010.
Serada et al., "Serum Leucine-rich Alpha-2 Glycoprotein Is a Disease Activity Biomarker in Ulcerative Colitis," *Inflamm Bowel Dis* 18(11):2169-2179, 2012.

* cited by examiner

*Primary Examiner* — Sean McGarry
(74) *Attorney, Agent, or Firm* — Seed IP Law Group LLP

(57) ABSTRACT

Provided are a novel prophylactic and/or therapeutic drug for an inflammatory disease and a method for searching for the same.
A prophylactic and/or therapeutic agent for an inflammatory disease that comprises a substance capable of inhibiting the expression or function of leucine rich alpha 2 glycoprotein (LRG). A method of screening for an anti-inflammatory substance using LRG or an LRG-expressing cell, wherein the inhibition of the expression or function of LRG is used as an index.

5 Claims, 2 Drawing Sheets the text file is 10.4 KB, was created on Oct. 6, 2015, and is being submitted electronically via EFS-Web.

PROPHYLACTIC AND/OR THERAPEUTIC AGENT FOR INFLAMMATORY DISEASE, AND METHOD FOR SCREENING PROPHYLACTIC AND/OR THERAPEUTIC DRUG FOR INFLAMMATORY DISEASE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690188_401USPC_SEQUENCE_LISTING.txt. The text file is 10.4 KB, was created on Oct. 6, 2015, and is being submitted electronically via EFS-Web.

TECHNICAL FIELD

The present invention relates to a prophylactic and/or therapeutic agent for an inflammatory disease such as ulcerative colitis or rheumatoid arthritis and a method for screening a prophylactic and/or therapeutic drug for an inflammatory disease. More specifically, the present invention relates to a prophylactic agent and/or a therapeutic agent for an inflammatory disease, comprising a substance for inhibiting the function of a leucine rich alpha 2 glycoprotein and a method for screening candidate substances of a prophylactic and/or therapeutic drug for an inflammatory disease using the inhibition of the function of a leucine rich alpha 2 glycoprotein as an indicator.

BACKGROUND ART

The inventors have previously reported that a blood leucine rich alpha 2 glycoprotein (LRG) (hereinafter, also referred to as LRG) concentration can be used as a disease marker for inflammatory diseases such as ulcerative colitis, Crohn's disease, rheumatoid arthritis, Behcet's disease, and Castleman's disease, and LRG can be an excellent disease activity marker because LRG has a higher correlation with disease activity thereof than C-reactive proteins (hereinafter, also referred to as CRP), which have been used as in inflammation marker (Patent Literature 1, Non-patent Literatures 1 and 2).

However, the function of LRG in the above-described diseases has yet to be elucidated. It was completely unknown whether LRG can be a therapeutic target for inflammatory diseases such as ulcerative colitis and rheumatoid arthritis.

CITATION LIST

Patent Literature

[PTL 1] Japanese Laid-Open Publication No. 2010-286279

Non Patent Literature

[NPL 1] Serada S et al., Ann Rheum Dis, Vol. 69, pages 770-774, 2010
[NPL 2] Serada S et al., Inflamm Bowel Dis, Vol. 18, pages 2169-2179, 2012

SUMMARY OF INVENTION

Technical Problem

Thus, the objective of the present invention is to elucidate the function of LRG in inflammatory diseases including ulcerative colitis and rheumatoid arthritis and to provide a prophylactic and/or therapeutic agent for such inflammatory diseases targeting LRG based on the aforementioned function, and to provide a means for searching for a novel substance having a prophylactic and/or therapeutic activity on an inflammatory diseases with function regulation of LRG as an indicator.

Solution to Problem

To achieve the above-described objective, the inventors induced colitis using dextran sulfate sodium (DSS) in LRG knockout mice and compared the pathology with that of a DSS colitis model of wild type mice. As a result, the LRG knockout mice recovered quicker from weight loss due to DSS administration as compared to wild type mice, while truncation of the large intestine was not observed. Furthermore, arthritis (CAIA) was induced in LRG knockout mice by administrating an anti-type II collage antibody cocktail. This resulted in a lower arthritis sore in the LRG knockout mice group in comparison to the wild-type mice. The results demonstrate that LRG is involved in the deterioration in the pathological condition of inflammatory diseases, including inflammatory bowel diseases and arthritis.

The inventors have completed the present invention as a result of further examinations based on such knowledge.

Specifically, the present inventions are as follows:

[1] A prophylactic and/or therapeutic agent for an inflammatory disease, comprising a substance for inhibiting the expression or function of a leucine rich alpha 2 glycoprotein (LRG)

[2] The agent of the above-described [1], wherein the substance for inhibiting the expression of LRG is
(a) an antisense nucleic acid to a transcription product of an LRG gene,
(b) a ribozyme nucleic acid to a transcription product of an LRG gene, or
(c) a nucleic acid having RNAi activity against a transcription product of an LRG gene or a precursor thereof.

[3] The agent of the above-described [1], wherein the substance for inhibiting the function of LRG is an antibody against LRG.

[4] The agent of any one of the above-described [1]-[3], wherein the inflammatory disease is an inflammatory bowel disease or an inflammatory autoimmune disease.

[5] A method of screening an anti-inflammatory substance, comprising the following steps (1)-(3):
(1) contacting a cell comprising an LRG gene or a nucleic acid encoding a reporter protein under control of a transcriptional regulatory domain of the LRG gene to a test substance;
(2) measuring an amount of expression of an LRG gene or an LRG protein or a reporter protein in the cell; and
(3) selecting, as a candidate anti-inflammatory substance, a test substance that has decreased the amount of expression of an LRG gene or an LRG protein or a reporter protein in comparison to a case where a measurement is taken in the absence of the test substance.

[6] A method of screening an anti-inflammatory substance, characterized by contacting LRG with a test substance and selecting, as a candidate anti-inflammatory substance, a test substance having an ability to bind to LRG.

[7] The method of screening of the above-described [6], comprising the following steps (1)-(3):
(1) contacting LRG with a fraction of a cell membrane of a target cell of an inflammatory disease in the presence of the test substance;

(2) measuring an amount of LRG bound to the fraction of a cell membrane; and
(3) selecting, as a candidate anti-inflammatory substance, a test substance that has decreased the amount of LRG binding to the fraction of a cell membrane in comparison to a case where a measurement is taken in the absence of the test substance.
[8] The method of the above-described [6] or [7], further comprising applying the test substance selected as the candidate anti-inflammatory substance to an inflammation model to test whether an inflammatory reaction is suppressed in the model.
[9] A method of screening for an anti-inflammatory substance, comprising the following steps (1)-(3):
(1) contacting a target cell of an inflammatory disease to a test substance in the presence and absence of LRG;
(2) measuring an extent of an inflammatory reaction in the cell under each condition; and
(3) selecting, as a candidate substance that inhibits the function of LRG and exhibits anti-inflammatory action, a test substance, which has suppressed an inflammatory reaction in the presence of LRG and has not suppressed an inflammatory reaction in the absence of LRG, compared to a case where a measurement is taken in the absence of the test substance.
[10] The method of the above-described [9], further comprising eliciting an inflammatory reaction in a target cell.
[11] The method of the above-described [10], characterized by eliciting an inflammatory reaction by a TNF alpha or $H_2O_2$ stimulation.
[12] The method of any one of the above-described [9]-[11], wherein a target cell is an intestinal epithelial cell or a synovial cell.

Advantageous Effects of Invention

The present invention has elucidated that LRG is involved in the deterioration in pathological conditions of inflammatory diseases including inflammatory bowel diseases and arthritis. Thus, it is possible to treat or prevent an inflammatory disease by inhibiting the expression or function of LRG. Further, it is possible to screen anti-inflammatory substances and consequently therapeutic and/or prophylactic drugs of an inflammatory disease, with inhibition of the expression or function of LRG as an indicator.

DESCRIPTION OF EMBODIMENTS

Figure 1:
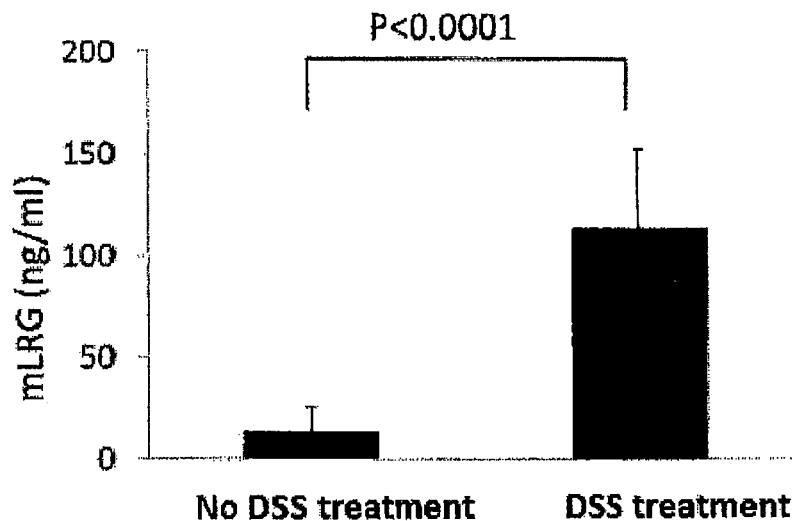
FIG. 1 is a diagram showing that the serum LRG (mLRG) concentration increases more in wild-type mice in which colitis is induced with dextran sulfate sodium (DSS) as compared to the DSS non-treatment group.

The present invention is at least partially based on the discovery that LRG contributes to the exacerbation of inflammatory diseases including inflammatory bowel diseases. The knowledge indicates that LRG not only can be used as an inflammation marker, but can also be a target of drug discovery for inflammatory diseases. That is, known inhibitory agents of LRG are useful in the prevention and/or treatment of inflammatory diseases. In addition, an LRG protein or cell or animal expressing the protein can be used to search for a substance that could be a novel LRG inhibitory agent and consequently a prophylactic and/or therapeutic drug for an inflammatory disease.

1. LRG or Nucleic Acid Encoding LRG

As used herein, LRG is a known protein comprising the amino acid sequence of human or murine LRG set forth in SEQ ID NO: 2 or 4 known as Genbank Accession No.: N_443204 or Genbank Accession No.: NP_084072, or an amino acid sequence that is substantially identical thereto. Proteins and peptides are described herein in accordance with the conventional denotation of peptides, where the left end is the N-terminal (amino terminal) and the right end is the C-terminal (carboxyl terminal).

Herein, LRG may be isolated from or purified by a known protein separation or purification technique from a cell (e.g., neutrophil or the like) or tissue (e.g., blood or the like) of a human or other warm-blooded animal (e.g., mouse, rat, bovine, monkey, dog, pig, sheep, rabbit, guinea pig, hamster, chicken, or the like).

The "amino acid sequence set forth in SEQ ID NO: 2 or an amino acid substantially identical thereto" includes the following (a) to (e):
(a) the amino acid sequence set forth in SEQ ID NO: 2;
(b) the amino acid sequence set forth in SEQ ID NO: 2 having a deletion, addition, insertion or substitution of one or a plurality of amino acids and imparting activity to promote an inflammatory reaction;
(c) an amino acid sequence having 90% or more homology to the amino acid sequence set forth in SEQ ID NO: 2 and imparting activity to promote an inflammatory reaction;
(d) an amino acid sequence encoded by DNA having the base sequence set forth in SEQ ID NO: 1; and
(e) an amino acid sequence, which is encoded by DNA that hybridizes with DNA having a complementary strand sequence of the base sequence set forth in SEQ ID NO: 1 under stringent conditions and imparts activity to promote an inflammatory reaction.

Specifically, "amino acid sequence set forth in SEQ ID NO: 2 or an amino acid substantially identical thereto" includes amino acid sequences of an ortholog of a human LRG protein in another mammal consisting of the amino acid sequence set forth in SEQ ID NO: 2 and amino acid sequences in a splice variant, allelic variant, or polymorphic variant of a human LRG protein consisting of the amino acid sequence set forth in SEQ ID NO: 2 or an ortholog thereof.

As used herein, "homology" refers to the ratio (%) of identical amino acid and similar amino acid residues with respect to all amino acid residues that overlap in the optimal alignment when aligning two amino acid sequences using a known mathematical algorithm in the art (preferably, the algorithm can take into consideration the introduction of a gap to one or both of the sequences for the optimal alignment). An "similar amino acid" refers to an amino acid that is similar in terms of a physicochemical property, including amino acids classified into the same group, such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), amino acids having a hydroxyl group (Ser, Thr), amino acids with a small side chain (Gly, Ala, Ser, Thr, Met), and the like. Substitutions by such similar amino acids are not expected to bring about a change in the phenotype of a protein (i.e., conservative amino acid substitution). Specific examples of a conservative amino acid substitution are well known in the art and described in various documents (for example, see Bowie et al., Science, 247:1306-1310 (1990)).

Homology of amino acid sequences herein can be calculated by using the homology calculation algorithm NCBI BLAST (National Center for Biotechnology Information Basic Local Alignment Search Tool) under the following conditions (expected value=10; allow gap; matrix=BLOSUM62; filtering=OFF). Examples of other algorithms for determining homology of amino acid sequences include the algorithm described in Karlin et al., Proc. Natl. Acad. Sci. USA, 90: 5873-5877 (1993) [said algorithm is incorporated into NBLAST and XBLAST program (version 2.0) (Altschul et al., Nucleic Acids Res., 25: 3389-3402 (1997))], the algorithm described in Needleman et al., J. Mol. Biol., 48: 444-453 (1970) [said algorithm is incorporated into the GAP program in the GCG software package], the algorithm described in Myers and Miller, CABIOS, 4: 11-17 (1988) [this algorithm is incorporated in the ALIGN program (version 2.0), which is a part of the CGC sequence alignment software package], the algorithm described in Pearson et al., Proc. Natl. Acad. Sci. USA, 85: 2444-2448 (1988) [this algorithm is incorporated into the FASTA program in the GCG software package] and the like, which may also be preferably used.

Examples of the stringent conditions in (e) described above include the conditions described in Current Protocols in Molecular Biology, John Wiley & Sons, 6.3.1-6.3.6, 1999, e.g., hybridization with 6×SSC (sodium chloride/sodium citrate)/45° C. followed by washing once or more times with 0.2×SSC/0.1% SDS/50-65° C. Those skilled in the art can appropriately select a hybridization condition providing similar stringency.

More preferably, an "amino acid sequence substantially identical to the amino acid sequence set forth in SEQ ID NO: 2" includes amino acid sequences having about 90% or higher identity, preferably about 95% or higher identity, more preferably about 96% or higher identity, still more preferably about 97% or higher identity, especially preferably about 98% or higher identity, and most preferably about 99% or higher identity with the amino acid sequence set forth in SEQ ID NO: 2.

A "protein comprising an amino acid sequence substantially identical to the amino acid sequence set forth in SEQ ID NO: 2" is a protein comprising an amino acid sequence substantially identical to the amino acid sequence set forth in SEQ ID NO: 2 and having a substantially the same function as a protein consisting of the amino acid sequence set forth in SEQ ID NO: 2.

In this regard, "substantially the same function" refers to having qualitatively the same property, for example, from a physiological or pharmacological viewpoint, but a quantitative element such as the extent of the function (e.g., about 0.1 to about 10 fold, preferably 0.5 to 2-fold) or the molecular weight of the protein may be different. Further, the detailed role of LRG in vivo is currently unknown. However, a protein having activity to promote an inflammatory reaction can be considered a "protein having a substantially the same function".

In this regard, activity to promote an inflammatory reaction can be measured, for example, by using an in vitro or in vivo inflammation (inflammatory disease) model discussed below.

Examples of LRG proteins in the present invention also include proteins containing (i) an amino acid sequence with 1-30 amino acids, preferably 1-10 amino acids, and more preferably 1-several (5, 4, 3, or 2) amino acids knocked out in the amino acid sequence set forth in SEQ ID NO: 2, (ii) an amino acid sequence with 1-30 amino acids, preferably 1-10 amino acids, and more preferably 1-several (5, 4, 3, or 2) amino acids added to the amino acid sequence set forth in SEQ ID NO: 2, (iii) an amino acid sequence with 1-30 amino acids, preferably 1-10 amino acids, and more preferably 1-several (5, 4, 3, or 2) amino acids inserted into the amino acid sequence set forth in SEQ ID NO: 2, (iv) an amino acid sequence with 1-30 amino acids, preferably 1-10 amino acids, and more preferably 1-several (5, 4, 3, or 2) amino acids substituted with other amino acids in the amino acid sequence set forth in SEQ ID NO: 2, or (iv) an amino acid sequence of a combination thereof and the like.

When an amino acid sequence has an insertion, deletion, addition, or substitution as described above, the position of the insertion, deletion, addition, or substitution is not particularly limited as long as the protein can promote an inflammatory reaction.

In this regard, examples of a method of artificially performing a deletion, addition, insertion, or substitution of an amino acid include conventional methods of introducing a site specific mutation into DNA encoding the amino acid sequence set forth in SEQ ID NO: 2 and then expressing the DNA with a common method. In this regard, examples of the method of introducing a site specific mutation include a method utilizing an amber mutation (gapped duplex method, Nucleic Acids Res., 12, 9441-9456(1984)) and a PCR method using a primer for introducing a mutation.

Preferred examples of LRG include human proteins consisting of human protein consisting of the amino acid sequence set forth in SEQ ID NO: 2 (Genbank Accession No. NP_443204), and orthologs allelic variants, polymorphic variant [e.g., single nucleotide polymorphisms (SNPs)] and the like thereof in other mammals (e.g., murine LRG protein (SEQ ID NO: 4, Genbank Accession No. NP_084072) and the like).

A "nucleic acid encoding LRG" represents a nucleic acid comprising a base sequence encoding the amino acid sequence set forth in SEQ ID NO: 2 shown in the above-described (a)-(e) or an amino acid sequence substantially identical thereto. Specifically, a "nucleic acid encoding LRG" includes nucleic acids having the following (f) to (j):

(f) a base sequence encoding the amino acid sequence set forth in SEQ ID NO: 2;

(g) a base sequence encoding an amino acid sequence with one or a plurality of amino acid deletions, additions, insertions, or substitutions in the amino acid sequence set forth in SEQ ID NO: 2 and imparting activity to promote an inflammatory reaction;

(h) a base sequence encoding an amino acid sequence having 90% of higher homology with the amino acid sequence set forth in SEQ ID NO: 2 and imparting activity to promote an inflammatory reaction;

(i) the base sequence set forth in SEQ ID NO: 1; or (j) a base sequence, which hybridizes with DNA having a complementary strand sequence of the base sequence set forth in SEQ ID NO: 1 under stringent conditions and encodes an amino acid sequence imparting activity to promote an inflammatory reaction.

In this regard, a gene may be either DNA such as cDNA or genomic DNA or RNA such as mRNA. A gene is a concept including both single stranded and double stranded nucleic acid sequences. Further, nucleic acid sequences set forth in SEQ ID NO: 1, SEQ ID NO: 3 and the like herein are DNA sequences for convenience. However, when an RNA sequence such as mRNA is represented, thymine (T) is understood as uracil (U).

Preferred examples of a nucleic acid encoding LRG include human LRG cDNA consisting of the base sequence set forth in SEQ ID NO: 1 (Genbank Accession No. NM_052972), and orthologs, allelic variants, polymorphic variants [e.g., single nucleotide polymorphisms (SNPs)] and the like thereof in other mammals (e.g., murine LRG cDNA (SEQ ID NO: 3, Genbank Accession No. NM_029796) and the like).

The present invention provides a prophylactic and/or therapeutic agent for an inflammatory disease, which does not comprise a substance that inhibits the expression or function of LRG.

II. Substance that Inhibits the Expression of LRG

In the present invention, a "substance that inhibits the expression of LRG" may be a substance that acts at any stage, such as the transcription level of a nucleic acid encoding LRG (LRG gene), the regulation level after transcription, the translation level to an LRG protein, modification level after the translation or the like. Thus, examples of a substance that inhibits the expression of LRG include substances that inhibit the transcription of an LRG gene (e.g., antigene), substances that inhibit the processing from an initial transcription product to mRNA, substances that inhibit the transport of mRNA to the cytoplasm, substances that inhibit the translation of mRNA to LRG (e.g. antisense nucleic acid, miRNA) or decompose mRNA (e.g., siRNA, ribozyme), substances that inhibit the modification after the translation of an initial translation production. A substance that acts at any stage can be preferably used. However, examples of more preferable substances are those selected from the group consisting of the following (1)-(3):

(1) antisense nucleic acids to a transcription product of an LRG gene;

(2) ribozyme nucleic acids to a transcription product of an LRG gene; and (3) nucleic acids having RNAi activity against a transcription product of an LRG gene or a precursor thereof.

In this regard, preferable examples of a transcription product include mRNA.

Preferred substances that specifically inhibit the translation of mRNA of an LRG gene to LRG (or decompose mRNA) include nucleic acids comprising a base sequence which is complementary or substantially complementary to the base sequence of mRNA or a portion thereof.

A base sequence substantially complementary to the base sequence of mRNA of an LRG gene refers to base sequences having a level of complementarity capable of binding to the target sequence of the mRNA and inhibiting the translation thereof (or cleaving the target sequence) under physiological conditions of an LRG producing cell (e.g., neutrophil) in a mammal subjected to administration, which are specifically, for example, base sequences having about 90% or higher homology, preferably about 95% or higher homology, and more preferably about 97% or higher homology to a base sequence that is completely complementary to the base sequence of said mRNA (i.e., base sequence of a complementary strand of mRNA) with respect to an overlapping region.

"Homology of base sequences" in the present invention can be calculated by using the homology calculation algorithm NCBI BLAST (National Center for Biotechnology Information Basic Local Alignment Search Tool) under the following conditions (expected value=10; allow gap; filtering=ON; match score=1; mismatch score=−3).

More specifically, a base sequence that is complementary or substantially complementary to the base sequence of mRNA of an LRG gene includes the following (k) to (l):

(k) a base sequence that is complementary or substantially complementary to the base sequence set forth in SEQ ID NO 1; and (l) a base sequence that hybridizes to a complementary strand sequence of the base sequence set forth in SEQ ID NO: 1 under stringent conditions and is complementary or substantially complementary to a sequence encoding a protein having activity to promote an inflammatory reaction.

Stringent conditions are as discussed above.

Preferred examples of mRNA of an LRG gene include mRNA of a human LRG comprising the base sequence set forth in SEQ ID NO: 1 (Genbank Accession No. NM_052972), orthologs thereof in other mammals (e.g., murine LRG (SEQ ID NO: 3, Genbank Accession No. NM_029796) and the like), and splice variants, allelic variants, and polymorphic variants thereof.

A "portion of a base sequence complementary or substantially complementary" to the base sequence of mRNA of an LRG gene is not particularly limited in terms of the length or position thereof as long as it can specifically bind to the mRNA of an LRG gene and inhibit the translation of a protein from said mRNA (or decompose said mRNA). However, in terms of sequence specificity, said portion comprises at least 10 bases, preferably about 15 bases or more of a portion complementary or substantially complementary to a target sequence.

Specifically, preferred examples of nucleic acids comprising a base sequence complementary or substantially complementary to the base sequence of mRNA of an LRG gene or a portion thereof include the following (1)-(3):

(1) antisense nucleic acids to mRNA of an LRG gene;

(2) ribozyme nucleic acids to mRNA of an LRG gene; and (3) nucleic acids having RNAi activity against mRNA of an LRG gene and precursors thereof.

(1) Antisense Nucleic Acid to mRNA of LRG Gene

The "antisense nucleic acids to mRNA of an LRG gene" in the present invention are nucleic acids comprising a base sequence complementary or substantially complementary to the base sequence of said mRNA or a portion thereof, the nucleic acids having a function to suppress protein synthesis by forming a specific and stable double strand with, and binding to, target mRNA.

Examples of antisense nucleic acids include polydeoxyribonucleotides containing 2-deoxy-D-ribose polyribonucleotide containing D-ribose, polynucleotides of other types, which are N-glycoside of a purine or pyrimidine base, other polymers having a non-nucleotide backbone (e.g., commercially available protein nucleic acids and synthetic sequence specific nucleic acid polymers), other polymers having a special bond (provided that said polymers contain a nucleotide with a sequence allowing adhesion of a base or base pairing as found in DNA or RNA) and the like. They may be double stranded DNA, single stranded DNA, double stranded RNA, single stranded RNA, or a DNA:RNA hybrid. Furthermore, antisense nucleic acids may be a non-modified polynucleotide (or a non-modified oligonucleotide), those added with a known modification, e.g., those with a label known in the art, those with a cap, those that are methylated, those with a substitution of one or more natural nucleotides with something similar, those with an intramolecular nucleotide modification, e.g., those with an uncharged bond (e.g., methyl phosphonate, phosphotriester, phosphoramidate, carbamate or the like), those with a charged bond or sulfur-containing bond (e.g., phosphorothioate, phosphorodithioate, or the like), e.g., those with a side chain group such as a protein (e.g., nuclease, nuclease inhibitor, toxin, antibody, signal peptide, poly-L-lysine or the like), a saccharide (e.g., monosaccharide) or the like, those with an intercalated compound (e.g., acridine, psoralen or the like) those containing a chelate compound (e.g., metal, metal with radiation activity, boron, oxidizing metal or the like), those containing alkylating agent, or those with a modified bond (e.g., alpha anomeric form nucleic acid and the like). In this regard, "nucleoside", "nucleotide" and "nucleic acid" may contain not only a purine and pyrimidine base, but also another modified heterocyclic base. Such a modified product may comprise a methylated purine and pyrimidine acylated purine and pyrimidine, or another heterocycle. A modified nucleoside and a modified nucleotide may have a modified saccharide portion. For example, one or more hydroxyl groups may be substituted with halogen, aliphatic group or the like, or converted into a functional group such as ether or amine.

As described above, antisense nucleic acids may be DNA, RNA, or a DNA/RNA chimera. When an antisense nucleic acid is DNA, an RNA:DNA hybrid formed with target RNA and antisense DNA can be recognized by endogenous RNase H to induce selective decomposition of the target RNA. Thus, for antisense DNA directing decomposition by RNase H, a target sequence may not only be a sequence in mRNA, but also a sequence of an intron region in an initial translation product of an LRG gene. An intron sequence can be determined by comparing a genomic sequence with a cDNA base sequence of an LRG gene by using a homology searching program such as BLAST or FASTA.

A target region of an antisense nucleic acid of the present invention is not particularly limited in length, as long as the antisense nucleic acid, when hybridized, results in the inhibition of translation to protein: LRG. The target region may be the entire sequence or a partial sequence of mRNA encoding LRG. A short target region includes those with about 10 bases, and long target region includes the entire sequence of an initial transcription product or mRNA. Considering the ease of synthesis, antigenicity, issues in intracellular migration, or the like, a target region is preferably an oligonucleotide consisting of about 10 to about 40 bases and especially about 15 to about 30 bases, but the length is not limited thereto. Specifically, a preferred target region of an antisense nucleic acid can be selected from, but is not limited, 5' end hairpin loop of an LRG gene, 5' end 6-base pair repeat, 5' end untranslated region, translation start codon, protein coding region, ORF translation stop codon, 3' end untranslated region, 3' end palindrome region, 3' end hairpin loop, and the like.

Furthermore, the antisense nucleic acid of the present invention may be those that not only can hybridize with an initial transcription product or mRNA of an LRG gene to inhibit translation to a protein, but also can bind to these genes that are double stranded DNA to form a triple strand (triplex) to inhibit the transcription to RNA (antigene).

Nucleotide molecules constituting an antisense nucleic acid may be naturally occurring DNA or RNA, but they can comprise various chemical modifications in order to enhance stability (chemically and/or against an enzyme) or specific activity (affinity to RNA). For example, in order to prevent the decomposition by a hydrolase such as nuclease, a phosphoric acid residue (phosphate) of each nucleotide constituting an antisense nucleic acid can be substituted with a chemically modified phosphoric acid residue such as phosphorothioate (PS), methyl phosphonate, or phosphorodithionate. Further, a hydroxyl group at position 2' of a saccharide (ribose) of each nucleotide may be substituted with —OR(OR(R=$CH_3$(2'-O-Me), $CH_2CH_2OCH_3$(2'-O-MOE), $CH_2CH_2NHC(NH)NH_2$, $CH_2CONHCH_3$, $CH_2CH_2CN$, or the like). Furthermore, the base moiety (pyrimidine, purine) may be chemically modified. Examples thereof include introduction of a cationic functional group or methyl group to position-5 of a pyrimidine base, substitution of a carbonyl group at position-2 to thiocarbonyl, and the like.

The conformation of a sugar moiety of RNA is predominantly of 2 forms, C2'-endo (S form) and C3'-endo (N form). In single stranded RNA, they are present in equilibrium. However, when a double strand is formed, the conformation is locked into the N type. Therefore, it is also possible to preferably use BNA (LNA) (Imanishi, T. et al., Chem. Commun., 1653-9, 2002; Jepsen, J. S. et al., Oligonucleotides, 14, 130-46, 2004) and ENA (Morita, K. et al., Nucleosides Nucleotides Nucleic Acids, 22, 1619-21, 2003) which are RNA derivatives with the conformation of the sugar moiety locked into the N type by crosslinking the 2' oxygen and 4' carbon to impart strong bindability to the target RNA.

The antisense oligonucleotide of the present invention can be prepared by determining a target sequence of an initial transcription product or mRNA based on a genomic DNA sequence or cDNA sequence of an LRG gene and synthesizing a sequence complementary thereto by using a commercially available DNA/RNA automatic synthesizer (Applied Biosystems, Beckman, or the like). Further, each of the above-described antisense nucleic acids comprising various modifications can be chemically synthesized by a known method.

(2) Ribozyme Nucleic Acid to mRNA of LRG Gene

Other preferred examples of a nucleic acid comprising a base sequence complementary or substantially complementary to the base sequence of mRNA of an LRG gene or a portion thereof include ribozyme nucleic acids that can specifically cleave said mRNA inside a coding region. A "ribozyme", when narrowly defined, refers to RNA having enzymatic activity for cleaving a nucleic acid, but is used herein as a concept that also encompasses DNA, as long as it has sequence specific nucleic acid cleaving activity. The most versatile ribozyme nucleic acid includes self-splicing RNA found in infectious RNA such as viroids and virusoids, for which hammerhead type, hair pin type and the like are known. The hammerhead type exhibits enzymatic activity with about 40 bases. It is possible to specifically cleave only the target mRNA by having several bases each on both ends adjacent the portion with a hammerhead structure (about 10 bases in total) to be a sequence complementary to the desired cleavage site of the mRNA. This type of ribozyme nucleic acid, since only RNA is the substrate thereof, has an addition advantage in that it would not attack genomic DNA. When mRNA of an LRG gene is in the form of a double stranded structure by itself, a target sequence can be made into a single strand by using a hybrid ribozyme linked to an RNA motif from a viral nucleic acid that can specifically bind to an RNA helicase [Proc. Natl. Acad. Sci. USA, 98(10): 5572-5577 (2001)]. Furthermore, a ribozyme, when used in a form of an expression vector including DNA encoding the ribozyme, can be formed into a hybrid ribozyme further linked to a sequence modified from tRNA in order to promote migration of a transcription product into the cytoplasm [Nucleic Acids Res., 29(13): 2780-2788 (2001)].

(3) siRNA to mRNA of LRG Gene

Double stranded RNA consisting of oligoRNA complementary to mRNA of an LRG gene and a complementary strand thereof the so-called siRNA, is also defined herein to be encompassed as nucleic acids comprising a base sequence complementary or substantially complementary to the base sequence of mRNA of an LRG gene or a portion thereof. A phenomenon called RNA interference (RNAi), wherein mRNA complementary to short double stranded RNA is decomposed when the RNA is introduced into a cell, has been known in nematodes, insects, plants and the like. However, ever since it was confirmed that this phenomenon widely occurs in animal cells [Nature, 411(6836): 494-498 (2001)], the phenomenon has been commonly used as an alternative technique for the above-described antisense nucleic acids and ribozymes.

SiRNA can be designed in accordance with the rule proposed, for example, by Elbashir et al. (Genes Dev., 15, 188-200 (2001)) or Teramoto et al. (FEBS Lett. 579(13):p 2878-82 (2005)) based on cDNA sequence information of a target gene. A target sequence of siRNA generally has a length of 15-50 bases, preferably 19-49 bases, and more preferably 19-27 bases. The target sequence may be, for example, AA+(N)19 (base sequence of 19 bases following AA), AA+(N)21 (base sequence of 21 bases following AA), or A+(N)21 (base sequence of 21 bases following A).

The nucleic acid of the present invention may have an additional base at the 5' or 3' terminal. The length of the additional base is generally about 2-4 bases and 19 bases or more as the full length of siRNA. The additional base may be DNA or RNA. However, when DNA is used, stability of a nucleic acid can be enhanced in some cases. Examples of a sequence of such an additional base include, but not limited to, the sequences ug-3', uu-3, tg-3', tt-3', ggg-3', guuu-3', gttt-3', ttttt-3', uuuuu-3', and the like.

Further, siRNA may have a protrusion sequence (overhang) at the 3' terminal. Specifically, an example thereof is siRNA added with dTdT (dT represents a deoxythymidine residue of deoxyribonucleic acid). Further, the end portion may be a smooth end (blunt end) without any terminal addition.

Further, siRNA may have different number of bases in a sense strand and an antisense strand. An example thereof includes "aiRNA", in which the antisense strand has a protrusion sequence (overhang) at the 3' terminal and the 5' terminal. Typical aiRNA consists of an antisense strand with 21 bases and a sense strand with 15 bases, and both ends of the antisense strand have an overhang structure of 3 bases each (Sun, X. et al., Nature Biotechnology Vol 26 No. 12 p 1379, International Publication No. WO 2009/029688 pamphlet).

The position of a target sequence is not particularly limited. However, it is desirable that the target sequence be selected from a region other than 3'-UTR, and 5'-UTR and about 50 bases from the start codon. A homology searching software such as BLAST (http://www.ncbi.nlm.nih.gov/BLAST/) is used to examine whether a group of candidate target sequences selected based on the aforementioned rule or another rule has homology to sequences of 16-17 consecutive bases in mRNA other that the target to confirm specificity of the selected target sequence. For a target sequence whose specificity is confirmed, double stranded RNA consisting of a sense strand having a 3' terminal overhang of TT or UU in 19-21 bases after AA (or NA) and an antisense strand having a 3' terminal overhang of TT or UU and a sequence complementary to the 19-21 bases may be designed as siRNA. Further short hairpin RNA (shRNA), which is a precursor of siRNA, can be designed by appropriately selecting any linker sequence capable of forming a loop structure (for example, about 5-25 bases), and linking the aforementioned sense strand and antisense strand via the linker sequence.

Sequences of siRNA and/or shRNA can be searched by using search software available at no cost on various websites. Examples of such sites include, but are not limited to, the siRNA Target Finder (http://www.ambion.com/jp/techlib/misc/siRNA_finder.html) and insert design tool for pSilencer™ Expression Vector (http://www.ambion.com/jp/techlib/misc/psilencer_converter.html), both provided by Ambion, and GeneSeer (http://codex.cshl.edu/scripts/newsearchhairpin.cgi), provided by RNAi Codex.

Ribonucleoside molecules constituting siRNA may also be modified in a similar manner to the above-described antisense nucleic acid to enhance stability, specific activity, or the like. However, for siRNA, RNAi activity may be lost if all ribonucleoside molecules in naturally occurring RNA are replaced with modified molecules. Thus, it is necessary to introduce the minimum number of modified nucleosides that allow an RISC complex to function.

As a specific example of such a modification, a portion of nucleotide molecules constituting siRNA can be substituted with naturally occurring DNA or RNA with various chemical modifications in order to enhance stability (chemically and/or against an enzyme) or specific activity (affinity to RNA) (see Usman and Cedergren, 1992, TIBS 17, 34: Usman et al., 1994, Nucleic Acids Symp. Ser. 31, 163). For example, in order to prevent decomposition by a hydrolase such as nuclease, a phosphoric acid residue (phosphate) of each nucleotide constituting siRNA can be substituted with a chemically modified phosphoric acid residue such as phosphorothioate (PS), methyl phosphonate, or phosphorodithionate. Further, a hydroxyl group at position 2' of a saccharide (ribose) of each nucleotide may be substituted with —OR(R=$CH_3$ (2'-O-Me), $CH_2CH_2OCH_3$(2'-O-MOE), $CH_2CH_2NHC(NH)NH_2$, $CH_2CONHCH_3$, $CH_2CH_2CN$, or the like) or a fluorine atom (—F). Furthermore, the base moiety (pyrimidine, purine) may be chemically modified. Examples thereof include introduction of a cationic functional group or methyl group to position-5 of a pyrimidine base, substitution of a carbonyl group at position-2 to thiocarbonyl and the like. In addition, a modification method in the above-described antisense nucleic acid described in (1) can be used. Alternatively, a chemical modification (2'-deoxyfied, 2'-H) to substitute a portion of RNA in siRNA with DNA may be applied. Further, an artificial nucleic acid in which position-2' and position 4' of a saccharide (ribose) are cross-linked with —O—$CH_2$— to lock the conformation to N type may be used (LNA: Locked Nucleic Acid).

Further, a sense strand and an antisense strand constituting siRNA may be chemically bound, via a linker, to a ligand that specifically recognizes a receptor on a cell surface layer, peptide, sugar chain, antibody, lipid, positive charge, oligoarginine, Tat peptide, Rev peptide, or Ant peptide that molecular-structurally adsorb and penetrate a cell surface layer.

SiRNA can be prepared by synthesizing each of a sense strand and an antisense strand of a target sequence on mRNA with a DNA/RNA automatic synthesizer and allowing them to denature for about 1 minute at about 90 to about 95° C. in a suitable annealing buffer, and then annealing them for about 1 to about 8 hours at about 30 to about 70° C. Further, siRNA can also be prepared by synthesizing a short hairpin RNA (shRNA), which is a siRNA precursor, and cleaving the shRNA with a dicer.

A nucleic acid designed to be able to produce siRNA to mRNA of an LRG gene in vivo is also defined herein to be encompassed as a nucleic acid comprising a base sequence complementary or substantially complementary to the base sequence of mRNA of an LRG gene or a portion thereof. Such a nucleic acid includes expression vectors constructed to express shRNA or siRNA described above. ShRNA can be prepared by designing oligo RNA comprising a base sequence, wherein a sense strand and antisense strand of a target sequence on mRNA are linked by inserting therebetween a spacer sequence with a length (e.g., about 5-25 bases) that can form an appropriate loop structure, and synthesizing the oligo-RNA with a DNA/RNA automatic synthesizer. Vectors that express siRNA come in the tandem type or the stem loop (hairpin) type. The former is the type in which an expression cassette for a sense strand and an expression cassette for an antisense strand of siRNA are linked tandem, each strand being expressed in the cell and is annealed to form double-stranded siRNA (dsRNA). Meanwhile, the latter is the type in which an expression cassette for shRNA is inserted into a vector, the shRNA being expressed in the cell and undergoing processing by a dicer to form a dsRNA. Although a pol II promoter (for example, immediate-early promoter of CMV) may be used as the promoter, it is common practice to use a pol III promoter in order to allow accurate transcription of short RNA. Examples of a pol III promoter include mouse and human U6-snRNA promoter, human Hl-RNase P RNA promoter, human valine-tRNA promoter and the like. As a transcription termination signal, a sequence of 4 or more consecutive T residues is used.

A siRNA or shRNA expression cassette is then inserted into a plasmid vector or a virus vector. Virus vectors such as retrovirus, lentivirus, adenovirus, adeno-associated virus, herpesvirus, and Sendai virus, animal cell expression plasmids and the like are used as such a vector.

The above-described siRNA can be chemically synthesized by a common method using a DNA/RNA automatic synthesizer, such as 394 Applied Biosystems, Inc. synthesizer, based on nucleotide sequence information. Examples thereof include methods described in Caruthers et al., 1992, Methods in Enzymology 211, 3-19, Thompson et al., International Publication No. WO99/54459, Wincott et al., 1995, Nucleic Acids Res. 23, 2677-2684, Wincott et al., 1997, Methods Mol. Bio., 74, 59, Brennan et al., 1998, Biotechnol Bioeng., 61, 33-45, Usman et al., 1987 J. Am. Chem. Soc., 109, 7845, Scaringe et al., 1990 Nucleic Acids Res., 18, 5433, and U.S. Pat. No. 6,001,311 and the like. Specifically, synthesis can be performed by using a nucleic acid protecting group (e.g., dimethoxytrityl group at the 5' terminal) and a coupling group (e.g., phosphoramidite at the 3' terminal) that are known to those skilled in the art. That is, a protecting group at the 5' terminal is deprotected with an acid such as TCA (trichloroacetic acid) to perform a coupling reaction. After capping with an acetyl group, a condensation reaction is performed on the next nucleic acid. For siRNA including modified RNA or DNA, modified RNA (e.g., 2'-O-methylnucleotide, 2'-deoxy-2'-fluoronucleotide) may be used as a raw material. The conditions of a coupling reaction can be appropriately adjusted. Further, when introducing a phosphorothioate bond with a modified phosphoric acid binding moiety, a Beaucage's reagent (3H-1,2-benzodithiol-3-one1, 1-dioxide) can be used.

Alternatively, oligonucleotide can be separately synthesized and connected together by ligation or like after synthesis (Moore et al., 1992, Science 256, 9923; Draper et al. International Publication No. WO 93/23569; Shabarova et al., 1991, Nucleic Acids Research 19, 4247; Bellon et al., 1997, Nucleosides&Nucleotides, 16, 951; Bellon et al., 1997, Nucleosides&Nucleotides, Bellon et al., 1997, Bioconjugate Chem. 8, 204) or may be connected together by hybridization after synthesis and/or deprotection. SiRNA molecules can also be synthesized by a tandem synthesis method. That is, both siRNA strands are synthesized as single continuous oligonucleotide separated by a cleavable linker, and this is cleaved to produce separate siRNA fragments which are hybridized and purified. A linker may be a polynucleotide linker or a non-polynucleotide linker.

Synthesized siRNA molecules can be purified by using a method known to those skilled in the art. Examples thereof include a method of purification by gel electrophoresis, a method of purification using high-performance liquid chromatography (HPLC) and the like.

Another preferred example of a nucleic acid comprising a base sequence complementary or substantially complementary to the base sequence of mRNA of an LRG gene or a portion thereof include micro RNA (miRNA) which targets the mRNA. Examples of human miRNA targeting human LRG mRNA include has-miR-220b, has-miR-93, has-miR-95, and the like. MiRNA can also be prepared in accordance with the aforementioned methods described for siRNA.

A nucleic acid comprising a base sequence complementary or substantially complementary to the base sequence of mRNA of an LRG gene or a portion thereof can be supplied in a special form such as a liposome or microsphere or in an adduct form. Examples of adduct forms used include polycations such as polylysine, which act to neutralize the charge of a phosphoric acid group backbone, and hydrophobic compounds such as lipids that enhance the interaction with a cell membrane or increase the uptake of nucleic acids (e.g., phospholipid, cholesterol and the like). Examples of lipids preferred for addition include cholesterol and derivatives thereof (e.g., cholesterylchloroformate, cholic acid and the like). These can be attached to the 3' end or the 5' end of a nucleic acid via a base, a sugar or an intramolecular nucleoside bond. Other groups include a capping group disposed specifically at the 3' end or 5' end of a nucleic acid for preventing decompose by nucleases such as exonuclease and RNase. Such capping groups include, but are not limited to, hydroxyl group protecting groups known in the art, including glycols such as polyethylene glycol and tetraethylene glycol.

LRG expression inhibiting activity of such nucleic acids can be studied by using transformant introduced with a nucleic acid encoding LRG, in vivo or ex vivo LRG gene expression system, or an in vivo or ex vivo LRG protein translation system.

Substances inhibiting the expression of LRG in the present invention are not limited to the nucleic acids comprising a base sequence complementary or substantially complementary to the base sequence of mRNA of an LRG gene or a portion thereof as described above. Such substances may be other substances such as a low molecular weight compound, as long as the substance directly or indirectly inhibits the production of LRG. Such substances can be obtained, for example, by the screening method of the present invention discussed below.

III. Substance Inhibiting the Function of LRG

As used herein, "substance inhibiting the function of LRG" in the present invention may be any substance, as long as the substance inhibits the exertion of a function of LRG that has been functionally produced.

Specifically, examples of substance inhibiting the function of LRG include antibodies against LRG. Said antibody may be either a polyclonal antibody or a monoclonal antibody. Such antibodies can be manufactured in accordance with a known method of manufacturing an antibody or antisera. The isotype of an antibody is not particularly limited. Preferred examples thereof include IgG, IgM, and IgA, and especially preferably IgG. Further, said antibody is not particularly limited if it at least has a complementarity determining region (CDR) for specifically recognizing and binding a target antigen. The antibody may be a complete antibody molecule or, for example, a fragment of Fab, Fab' or F (ab')$_2$ or the like, a conjugate molecule that is made by genetic engineering such as scFv, scFv-Fc, minibody, or diabody, a derivative thereof modified with a molecule having protein stabilizing action such as polyethylene glycol (PEG) or the like.

In a preferred Embodiment, since an antibody to LRG is used as a medicament whose target of administration is human, said antibody (preferably a monoclonal antibody) is an antibody with reduced risk exhibiting antigenicity when administered to humans, specifically a fully human antibody, humanized antibody, murine-human chimeric antibody or the like, and especially preferably fully human antibody. Humanized antibodies and chimeric antibodies can be made by genetic engineering in accordance with a conventional method. Further, a fully human antibody can be manufactured with a human-human (or murine) hybridoma. However, it is desirable to manufacture such an antibody by using a human antibody producing mouse or a phase display method in order to provide a large amount of antibodies stably and at low cost.

Other preferred substances for inhibiting the function of LRG are low molecular weight compounds meeting Lipinski's Rule. Suh compounds can be obtained, for example, by using the screening method of the present invention discussed below.

Substances that inhibit the expression or function of LRG exhibit activity to suppress an inflammatory reaction promoted by LRG. Thus, as an anti-inflammatory agent, the substances are effective in the prevention and/or treatment of inflammatory diseases such as inflammatory bowel disease.

Thus, a medicament containing a substance inhibiting the expression or function of LRG can be used as a prophylactic and/or therapeutic agent (antiflammatory agent) for an inflammatory disease.

IV. Medicament Containing Antisense Nucleic Acid, Ribozyme Nucleic Acid, siRNA or a Precursor Thereof The antisense nucleic acid of the present invention that can complementarily bind to a transcription product of an LRG gene to suppress the translation of a protein from the transcription product, siRNA (or ribozyme) which has a base sequence that is homologous (or complementary) to a transcription product (mRNA) of an LRG gene and capable of cleaving the transcription product with said transcription product as a target, shRNA which is a precursor of the siRNA (hereinafter, also collectively referred to as the "nucleic acid of the present invention") suppress the expression of LRG in vivo and suppress an inflammatory reaction. Thus, the nucleic acid of the present invention can be used as an anti-inflammatory agent.

A medicament containing the nucleic acid of the present invention has low toxicity and can be administered orally or parenterally (e.g. intravascular administration, subcutaneous administration, etc.) to humans or non-human mammals (e.g., rats, rabbits, sheep, pigs, cows, cats, dogs, monkeys or the like) directly as a liquid agent or as a pharmaceutical composition with a suitable dosage form.

When using the nucleic acid of the present invention as the above-described anti-inflammatory agent, the nucleic acid can be formulated and administered in accordance with a known method. That is, the nucleic acid of the present invention can be inserted directly or into a suitable expression vector for a mammalian cell such as retrovirus vector, adenovirus vector, adenovirus-associated virus vector or the like in a functionable form and then formulated in accordance with a conventional means. Said nucleic acid can be administered directly or with an adjuvant for uptake promotion by a catheter such as a hydrogel catheter or a gene gun. Alternatively, the nucleic acid can be aerosolized and topically administered in the trachea as an inhalant.

Furthermore, the nucleic acid may be formulated (formed into an injection) and intravenously or subcutaneously administered alone or with a carrier such as a liposome in order to improve pharmacokinetics, extend the half-life, and improve intracellular uptake efficiency.

The nucleic acid of the present invention may be administered by itself, or administered as a suitable pharmaceutical composition. A pharmaceutical composition used in administration may those comprising the nucleic acid of the present invention and a pharmacologically acceptable carrier, diluent, or an excipient. Such a pharmaceutical composition is provided in a dosage form suitable for oral or parenteral administration.

For example, injections, suppositories or the like are used as a composition for parenteral administration, and the injections may include dosage forms such as subcutaneous injections, intracutaneous injections, intramuscular injections, intravenous infusions and the like. Such injections can be prepared in accordance with a known method. As an example of a preparation method of injections, injections can be prepared by dissolving, suspending, or emulsifying the above-described nucleic acid of the present invention into an oil-based solution or an aseptic aqueous solution that is generally used in an injection. For example, saline, isotonic solution comprising glucose or other adjuvant, or the like is used as an aqueous solution for injections, which may be used in conjunction with a suitable solubilizing agent, such as alcohol (e.g., ethanol), polyalcohol e.g., propylene glycol, polyethylene glycol), non-ionic surfactant (e.g., polysorbate 80, HCO-50 (polyoxyethylene (50 mol) adduct of hydrogenated castor oil)) or the like. For example, sesame oil, soybean oil or the like is used as an oil base solution, which may be used in conjunction with benzyl benzoate, benzyl alcohol or the like as a solubilizing agent. Prepared injections are preferably loaded in a suitable ampoule. Suppositories used in rectal administration may be prepared by mixing the above-described nucleic acid with a common base agent for suppositories.

Compositions for oral administration include solid and liquid forms, specifically tablets (including sugar coated tablets and film-coated tablets), pills, granules, powder, capsules (including soft capsules), syrups, emulsion, suspensions and the like. Such compositions are manufactured by a known method. The compositions may contain a carrier, diluent, or excipient that is commonly used in the field of drug formulations. Examples of carriers and excipients for tablets include lactose, starch, sucrose, and magnesium stearate.

It is advantageous to prepare the above-described parenteral or oral pharmaceutical composition to have a dosage form in a dosage unit that would match the dosage of the active ingredient. Examples of such dosage forms in a dosage unit include tablets, pills, capsules, injections (ampoule), and suppositories. The nucleic acid of the present invention is generally contained, for example, at 5-500 mg per dosage form in a dosage unit, and particularly preferable at 5-100 mg for injections and 10-250 mg in other dosage forms.

The dosage for the above-described medicaments containing the nucleic acid of the present invention, although varies depending on the subject of administration, target disease, symptom, route of administration or the like, is advantageously administrated by intravenous injection about 1-5 times daily and preferably about 1-3 times daily with generally about 0.01-20 mg/kg weight as a single dose of the nucleic acid of the present invention, or preferably about 0.1-10 mg/kg weight, or more preferably about 0.1-5 mg/kg weight when used for the treatment or prevention of inflammatory bowel diseases (IBD) such as ulcerative colitis (UC) or Crohn's disease (CD). For other parenteral administration and oral administration, an amount in accordance therewith can be administered. When the symptom is especially severe, the amount may be increased in accordance with the symptom.

Each of the aforementioned compositions may contain other suitable active ingredients as long as an unfavorable interaction does not occur due to mixing with the nucleic acid of the present invention.

V. Medicament Containing Antibody to LRG, Low Molecular Weight Compound that Inhibits the Expression of Function of LRG or the Like Antibodies to LRG and low molecular weight compounds that inhibit the expression or function of LRG can inhibit the production or function of LRG. Thus, since such substances inhibit the expression or function of LRG in vivo, the substances can be used as a prophylactic and/or therapeutic agent for an inflammatory disease.

A medicament containing the above-described antibody or a low molecular weight compound has low toxicity and can be administered orally or parenterally (e.g., intravascular administration, subcutaneous administration or the like) to humans or mammals (e.g., rats, rabbits, sheep, pigs, cows, cats, dogs, monkeys or the like) directly as a liquid agent or as a pharmaceutical composition with a suitable dosage form.

The above-described antibodies and low molecular weight compounds may be administered directly or as a suitable pharmaceutical composition. A pharmaceutical composition used in administration may comprise the above-described antibody or low molecular weight compound or a salt thereof and a pharmacologically acceptable carrier, diluent, or an excipient. Such a pharmaceutical composition is provided in a dosage form suitable for oral or parenteral administration.

For example, injections, suppositories or the like are used as a composition for parenteral administration. The injections may include dosage forms such as intravenous injections, subcutaneous injections, intracutaneous injections, intramuscular injections, and intravenous infusions. Such injections can be prepared in accordance with a known method. As an example of a preparation method of injections, injections can be prepared by dissolving, suspending, or emulsifying the above-described antibody, low molecular weight compound, or a salt thereof of the present invention into an oil-based solution or an aseptic aqueous solution that is generally used in an injection. For example, saline, isotonic solution comprising glucose or other adjuvant, or the like is used as an aqueous solution for injections, which may be used in conjunction with a suitable solubilizing agent, such as alcohol (e.g., ethanol), polyalcohol (e.g., propylene glycol, polyethylene glycol), non-ionic surfactant (e.g., polysorbate 80, HCO-50 (polyoxyethylene (50 mol) adduct of hydrogenated castor oil)) or the like. For example, sesame oil, soybean oil or the like is used as an oil base solution, which may be used in conjunction with benzyl benzoate, benzyl alcohol or the like as a solubilizing agent. Prepared injections are preferably loaded in a suitable ampoule. Suppositories used in rectal administration may be prepared by mixing the above-described antibody or a salt thereof with a common base agent for suppositories.

Compositions for oral administration include solid and liquid forms, specifically tablets (including sugar coated tablets and film-coated tablets), pills, granules, powder, capsules (including soft capsules), syrups, emulsion, suspensions and the like. Such compositions are manufactured by a known method. The compositions may contain a carrier, diluent, or excipient that is commonly used in the field of drug formulations. Examples of carriers and excipients for tablets include lactose, starch, sucrose, and magnesium stearate.

It is advantageous to prepare the above-described parenteral or oral pharmaceutical composition in a dosage form in a dosage unit that would match the dosage of active ingredient. Examples of such dosage forms in a dosage unit include tablets, pills, capsules, injections (ampoule), and suppositories. An antibody or low molecular weight compound is generally contained at 5-500 mg per dosage form in a dosage unit, and particularly preferable at 5-100 mg for injections and 10-250 mg in other dosage forms.

The dosage of the above-described medicaments containing the above-described antibody, low molecular weight compound, or a salt thereof, although varies depending on the subject of administration, target disease, symptom, route of administration or the like, is advantageously administered by intravenous injection about 1-5 times daily and preferably about 1-3 times daily with generally about 0.01-20 mg/kg weight as a single dose of the antibody, low molecular weight compound, or a salt thereof, or preferably about 0.1-10 mg/kg weight, or more preferably about 0.1-5 mg/kg weight when used for the treatment or prevention of IBD. For other parenteral administration and oral administration, an amount in accordance therewith can be administered. When the symptom is especially severe, the amount may be increased in accordance with the symptom.

Each of the aforementioned compositions may contain other active ingredients as long as an unfavorable interaction does not occur due to mixing with the above-described antibody or low molecular weight compound.

The medicaments containing an antisense nucleic acid, ribozyme nucleic acid, siRNA or a precursor thereof to LRG, and pharmaceutical compositions containing an antibody to LRG, a low molecular weight compound that suppresses the expression or function of LRG or the like discussed above can be used in the treatment or prevention of an inflammatory disease or prevent the progression thereof as an anti-inflammatory agent. Examples of specific inflammatory diseases include, but are not limited to, inflammatory bowel diseases (IBD) such as ulcerative colitis (UC) and Crohn's disease (CD), inflammatory autoimmune diseases such as rheumatoid arthritis (RA), Behcet's disease, and Castleman's disease, and the like. Any inflammation in which LRG is involved in the exacerbation of the pathological condition thereof is encompassed by the inflammatory disease targeted by the present invention.

The medicaments containing an antisense nucleic acid, ribozyme nucleic acid, siRNA or a precursor thereof to LRG, and pharmaceutical compositions containing an antibody to LRG, a low molecular weight compound that suppresses the expression or function of LRG or the like discussed above may be used alone in the treatment or prevention of an inflammatory disease, but may be used in conjunction with one or two or more agents having anti-inflammatory action.

Examples of the agent used in conjunction therewith, although not particularly limited, include mesalazine, corticosteroid (e.g., betamethasone, prednisolone, hydrocortisone, dexamethasone and the like), nonsteroidal anti-inflammatory drugs (NSAIDs; e.g., salicylic acid-based, anthracitic acid-based, aryl acid-based, propionic acid-based, oxicam-based, and pyrine-based drugs), anti-TNF alpha antibodies (infliximab and adalimumab), and anti-rheumatoid agents (e.g., immunomodulator such as actarit, immunosuppressant such as methotrexate, biological formulations such as anti-TNF alpha antibody and etanercept) and the like.

VI. Screening of Candidate Pharmaceutical Compounds for Disease

As discussed above, an inflammatory reaction is suppressed if the expression and/or function of LRG is inhibited. Thus, a compound that inhibits the expression and/or function of LRG can be used as a prophylactic and/or therapeutic agent (anti-inflammatory agent) for an inflammatory disease.

Thus, cells producing LRG can be used as a tool for screening anti-inflammatory substances by using the amount of expression and/or function of LRG (or LRG gene) as an indicator.

When screening for a compound that inhibits the expression or function of LRG, the screening method includes culturing cells having the ability to produce LRG in the presence and absence of a test substance and comparing the degree of the amount of expression or function of LRG under both conditions. Further, compounds that inhibit the function of LRG can also be screened by testing the ability to bind to a purified LRG protein or activity to inhibit the binding of an LRG protein to a binding protein thereof (e.g., LRG receptor).

Cells having the ability to produce LRG used in the above-described screening method are not particularly limited as long as they are cells of humans or other mammals that naturally express LRG or biological samples comprising such cells (e.g., blood, tissue, organ, or the like). Blood, tissue, organ or the like derived from a non-human animal may be isolated from an organism and cultured. Alternatively, a test substance may be administered to an organism itself and the biological sample may be isolated after a certain time has passed.

Further, examples of cells having an ability to produce LRG include various transformants created by a known conventional genetic engineering method. For example, animal cells such as H4IIE-C3 cells, HepG2 cells, HEK293 cells, COS7 cells, CHO cells or the like are preferably used as a host.

Specifically, DNA encoding LRG (i.e., DNA which hybridizes with the base sequence set forth in SEQ ID NO: 1 or a base sequence having complementarity thereto under stringent conditions and comprises a base sequence encoding a polypeptide having a similar function as a protein consisting of the amino acid sequence set forth in SEQ ID NO: 2) can be linked downstream of a promoter in an suitable expression vector and introduced into a host animal cell for the preparation thereof.

A method of preparing a gene encoding LRG is explained below.

A gene encoding LRG can be obtained in accordance with a common genetic engineering method (e.g., methods described in Molecular Cloning 2nd edition authored by Sambrook J., Frisch E. F. Maniatis T., Cold Spring Harbor Laboratory press and the like). That is, DNA encoding LRG, for example, can be obtained by synthesizing a suitable oligonucleotide as a probe or a primer based on the base sequence set forth in SEQ ID NO: 1 and cloning, from cDNA library or cDNA derived from a cell or tissue producing LRG described above, by using a hybridization method or PCR. Hybridization can be performed in accordance with a method described, for example, in Molecular Cloning 2nd Edition (described above) or the like. Further, when using a commercially-available library, hybridization can be performed in accordance with a method described in the instruction manual appended to the library.

The base sequence of DNA can be changed in accordance with a known method such as ODA-LA PCR, Gapped duplex method, Kunkel method or the like or a method corresponding thereto by using a known kit, such as Mutant™-super Express Km (Takara Shuzo Co. LTD) or Mutan™-K (Takara Shuzo Co. LTD).

Depending on the objective, cloned DNA can be used directly or, if desired, after digestion with a restriction enzyme or after adding a linker. The DNA may have ATG as a translation start codon at the 5' terminal side thereof and TAA, TGA or TAG as a translation stop codon on the 3' terminal side. These translation start codons and translation stop codons can be added by using a suitable synthetic DNA adaptor.

Next, LRG proteins can be manufactured/obtained in accordance with a common genetic engineering method by using the resulting LRG gene.

For example, LRG may be obtained from a culture obtained by creating a plasmid where an LRG gene can be expressed in a host cell and introducing the plasmid into and transforming the plasmid in a host cell, and culturing the transformed host cell (transformant). Preferred examples of the above-described plasmid include plasmids, which comprise genetic information that can be replicated in a host cell, are capable of autonomous replication, are readily isolated/purified from the host cell, have a promoter capable of functioning in the host cell, and have a gene encoding LRG introduced in an expression vector having a detect able marker. Various expression vectors are commercially available.

For example, expression vectors used in the expression in *E. coli* are expression vectors comprising a promoter such as lac, trp, or tac. Such expression vectors are commercially available from Pharmacia, Takara Bio, and the like. Restriction enzymes used for introducing a gene encoding LRG into the expression vector are also commercially available from Takara Rio and the like. When it is necessary to induce even higher expression, a ribosome binding region may be linked upstream of DNA encoding LRG. Ribosome binding regions that are used include those described in the report by Guarente L, et al. (Cell 20, p 543) or Taniguchi et al. (Genetics of Industrial Microorganisms, p 202, Kodansha).

Further, it is possible to use animal cell expressing plasmids (e.g.: pA1-11, pXT1, pRc/CMV, pRc/RSV, and pcDNAI/Neo); bacteriophages such as λ phage; animal virus vectors of a retrovirus, vaccinia virus, adenovirus or the like. A promoter may be any suitable promoter matching a host used in the expression of a gene. For example, an SR alpha promoter, SV40 promoter, LTR promoter, CMV (cytomegalovirus) promoter, RSV (Rous sarcoma virus) promoter, MoMuLV (Moloney murine leukemia virus) LTR, HSV-TK (herpes simplex virus thymidine kinase) promoter, beta-actin gene promoter, aP2 gene promoter or the like is used. Among such promoters, BE-alpha promoters, CAG promoters, CMV promoters, SR alpha promoters and the like are preferable.

Besides those described above, expression vectors containing an enhancer, splicing signal, poly-A addition signal, selection marker, SV40 replication origin (hereinafter, also abbreviated to as SV40 ori) or the like can be used if desired as an expression vector.

Examples of selection markers include dihydrofolate reductase gene (hereinafter, also abbreviated as dhfr; methotrexate (MTX) resistant), ampicillin resistant gene (hereinafter, also abbreviated as amp"), neomycin resistant gene (hereinafter, also abbreviated as neo"; G418 resistant) and the like. In particular, when a dhfr gene deficient Chinese hamster cells are used and the dhfr gene is used as a selection marker, a gene of interest can be selected by a thymidine-free medium.

LRG expressing cells can be manufactured by transforming a host with an expression vector comprising DNA encoding LRG described above.

Examples of host cells include microorganism cells that are prokaryotes or eukaryotes, insect cells, mammalian cells and the like. For example, HepG2 cells, HEK293 cells, HeLa cells, human FL cells, monkey COS-7 cells, monkey Vero cells, Chinese hamster ovary cells (hereinafter, abbreviated as CHO cells), dhfr gene deficient CHO cells (hereinafter, abbreviated as CHO (dhfr$^-$) cells), mouse L cells, mouse AtT-20 cells, mouse myeloma cells, rat H411E-C3 cells, rat GH3 cells or the like can be used as the mammalian cell. Preferred examples include E. coli from the viewpoint of facilitating mass preparation of LRG.

A plasmid obtained as described above can be introduced into the host cell by a common genetic engineering method. Culture of a transformant can be performed by a common method used in microorganism culture or culture of insect cells or mammalian cells. For example, E. coli is cultured in a medium appropriately comprising a small amount of suitable nutrients such as a carbon source, nitrogen source or vitamin. A culturing method may be either solid culture or liquid culture. Preferred examples include liquid culture such as aeration and agitation culturing method.

Transformation can be performed by a method such as calcium phosphate co-precipitation, PEG, electroporation, microinjection, or lipofection. For example, the method described in Saibokogaku Bessatsu 8 Shin-saibokogaku Jikken Purotokoru 263-267 (1995) (published by Shujunsha) or Virology, Vol. 52, 456 (1973) can be used.

Mammalian cells having the ability to produce natural LRG or transformed cells obtained as described above or tissue/organ comprising said cells can be cultured in a medium such as a minimum essential medium (MEM) comprising about 5-20% fetal bovine serum [Science, Vol. 122, 501 (1952)], Dulbecco's modified eagle's medium (DMEM) [Virology, Vol. 8, 396 (1959)], RPMI 1640 medium [The Journal of the American Medical Association, Vol. 199, 519 (1967)], or 199 medium [Proceeding of the Society for the Biological Medicine, Vol. 73, 1 (1950)]. The pH of a medium is preferably about 6-8. Culture is generally performed at about 30-40° C. and further aerated or agitated as needed.

LRG proteins may be obtained by combining methods commonly used in the isolation/purification of a common protein. For example, a transformant obtained by the aforementioned culture may be removed by centrifugation or the like and LRG may be purified as described above from culture supernatant. Further, when LRG proteins accumulate in a transformant cell obtained by the aforementioned culture, for example, said transformant is collected by centrifugation or the like, the cells are crushed or lysed, and the protein is solubilized if necessary and purified by a step using various chromatographies, such as ion exchange, draining, and gel filtering individually or in combination. Another operation to restore the conformation of the purified protein may be performed.

In implementing the screening of the present invention, examples of test substance include proteins, peptides, non-peptidic compounds, synthetic compounds, fermentation products, cell extract, plant extract, animal tissue extract and the like. Such substances may be novel or known.

Further, when selecting a substance that decreases the amount of expression of LRG gene or LRG or a substance that decreases the function of LRG, a control cells which are not contacted with a test substance can be used as a comparative control. In this regard, "is not contacted with a test substance" herein includes cases where a solvent (blank) in the same amount as a test substance is added instead of the test substance and cases where a negative control substance which does not affect the function of LRG or the amount of expression of LRG gene or LRG is added.

A test substance can be contacted with the above-described cell, for example, by adding the test substance in the above-described medium or various buffers (e.g., HEPES buffer, phosphate buffer, phosphate buffered saline, tris-hydrochloric acid buffer, borate buffer, acetate buffer and the like) and incubating the cell for a certain period of time. The concentration of added test substances, although varies depending on the type of compound (solubility, toxicity, or the like), is appropriately selected, for example, in the range of about 0.1 nM to about 100 pH. Examples of incubation time include about 10 minutes to about 24 hours.

When cells producing LRG are provided in a form of an individual non-human mammal, the condition of the individual animal is not particularly limited, but may be, for example, an inflammatory disease model animal in which an inflammation is induced by a drug or genetic modification (e.g., mice in which colitis is induced by a drug such as dextran sulfate sodium (DSS) or 2,4,6-trinitrobenzenesulfonate (TNBS), IBD model animals such as genetically modified mice such as IL-10 knockout mice or IL-2 knockout mice, RA model animals such as collagen induced arthritic (CIA) mice, SKG mice, PD-1 knockout mice, K/BxN mice, or synoviolin Tg mice). The rearing condition of the animals used is not particularly limited, but is preferably reared in an SPF grade or better environment. A test substance and the cells are contacted by administering the test substance to the individual animal. The route of administration is not particularly limited, but examples thereof include intravenous administration, intraarterial administration, subcutaneous administration, intracutaneous administration, intraperitoneal administration, oral administration, tracheobronchial administration, rectal administration and the like. The dosage is also not particularly limited, but for example, about 0.5-20 mg/kg can be administered as a single dose, 1-5 times daily, preferably 1-3 times daily, for 1-14 days.

Alternatively, the above-described screening method can be performed by contacting a test substance with, instead of cells having the ability to produce LRG, LRG that is isolated and purified from said cells or extract of said cells.

(Measurement of Amount of Expression of LRG or LRG Gene)

The present invention provides a method of screening for an anti-inflammatory substance, characterized by comparing the expression of said protein (gene) in cells having the ability to produce LRG in the presence and absence of a test substance. The cells, type of test substance, form of contact between the test substance and cells, and the like that are used in the present invention are the same as those described above.

The amount of expression of LRG can be measured with the RNA level by using a nucleic acid that can hybridize with DNA encoding LRG discussed above under stringent conditions, i.e., nucleic acid (DNA) that can hybridize with the base sequence set forth in SEQ ID NO: 1 or a base sequence that is complementary thereto under stringent conditions (hereinafter, also referred to as the "nucleic acid for detection of the present invention") to detect mRNA of an LRG gene. Alternatively, said amount of expression can be measured with the protein level by using an antibody to LRG described above (hereinafter, also referred to as the "antibody for detection of the present invention") to detect such proteins.

Thus, more specifically, the present invention provides (a) a method of screening for an anti-inflammatory substance, characterized by culturing a cell having the ability to produce LRG in the presence and absence of a test substance and measuring and comparing the amount of mRNA encoding said protein under both conditions by using the nucleic acid for detection of the present invention, and (b) a method of screening for an anti-inflammatory substance, characterized by culturing a cell having the ability to produce LRG in the presence and absence of a test substance and measuring and comparing the amount of said protein under both conditions by using the antibody for detection of the present invention.

That is, a substance that changes the amount of expression of LRG can be screened in the following manner.

(i) A test substance is administered to a normal or disease model (e.g., DSS or TNBS induced colitis model or the like) non-human mammal (e.g., mouse, rat, rabbit, sheep, pig, cow, cat, dog, monkey or the like), and blood or a certain organ (e.g. brain or the like), or tissue or cell isolated from an organ is obtained after a certain period of time has passed (after 30 minutes to 3 days, preferably after 1 hour to 2 days, and more preferably after one hour to 24 hours).

MRNA of LRG can be quantified by extracting mRNA from a cell or the like by a common method or by a known Northern blot analysis. Meanwhile, the amount of protein of LRG can be quantified by using a western blot analysis or various immunoassay methods that are discussed below in detail.

(ii) A cell expressing an LRG gene (e.g., transformant introduced with LRG) is made in accordance with the above-described method. A test substance is added to a medium or buffer when culturing in accordance with a conventional method. After incubating for a certain period of time (after 1 to 7 days, preferably after 1 to 3 days, and more preferably after 2 to 3 days), LRG contained in the cell culture or mRNA encoding said LRG can be quantified and analyzed as in the above-described (i).

The expression level of an LRG gene (mRNA) can be detected and quantified by a known method such as a northern blot method or RT-PCR by using RNA prepared from said cell or a complementary polynucleotide transcripted therefrom. Specifically, the presence of expression of an LRG gene in RNA or the expression level thereof can be detected or measured by using a polynucleotide having at least 15 consecutive bases in a base sequence of an LRG gene and/or a polynucleotide that is complementary thereto as a primer or a probe. Such a probe or primer can be designed by utilizing, for example, primer 3 (http://primer3.sourceforge.net/) or Vector NTI (Infomax) based on a base sequence of an LRG gene.

When a northern blot method is used, an example thereof includes a method of labeling the primer or probe with a radioisotope ($^{32}P$, $^{33}P$, or the like: RI), a fluorescent substance or the like and hybridizing the primer or primer with RNA derived from a cell transferred to a nylon membrane or the like in accordance with a conventional method, and then detecting and measuring the formed double strand of RNA and the primer or probe (DNA or RNA) with a radiation detector (BAS-1800II, Fuji Film) or a fluorescence detector as a signal from a label (RI or fluorescent substance) of the primer or probe. Further, it is also possible to use a method of using AlkPhos Direct Labelling and Detection System (Amersham Pharamcia Biotech), labeling the probe in accordance with the protocol and hybridizing the probe with RNA derived from a cell, and detecting and measuring a signal from a label of the probe with a Multi Bio Imager STORM 860 (Amersham Pharmacia Biotech).

When using RT-PCR, example thereof includes a method of preparing cDNA in accordance with a conventional method from RNA derived from a cell, hybridizing a pair of primers (plus strand that binds to the above-described cDNA (single strand), minus strand that binds to+strand) prepared based on the sequence of an LRG gene therewith so that a target LRG gene region can be amplified with the cDNA as a template, and performing PCR in accordance with a conventional method to detect the resulting amplified double strand DNA. The detection of amplified double strand DNA can use a method of detecting labeled double strand DNA produced by performing the above-described PCR using a primer that is labeled in advance with RI or a florescent substance, a method of transferring the produced double strand DNA to a nylon membrane or the like in accordance with a conventional method and using the labeled primer as a probe for hybridization with the DNA for detection. Produced labeled double strand DNA products can be measured by an Agilent 2100 Bioanalyzer (Yokogawa Analytical Systems) or the like. Further, it is also possible to prepare an RT-PCR reaction solution with SYBR Green RT-PCR Reagents (Applied Biosystems) in accordance with the protocol, and reacting the solution with ABI PRIME 7900 Sequence Detection System (Applied Biosystems) to detect the reactant.

If expression of an LRG gene in a cell to which a test substance is added is ⅔ or less, preferably ½ or less, and more preferably ⅓ or less in comparison to the amount of expression in a control cell to which the test substance is not added, the test substance can be selected as a substance suppression the expression of an LRG gene.

Further, a substance that changes the amount of expression of LRG can be screened for by a reporter gene assay using a transcriptional regulatory domain of an LRG gene. A "transcriptional regulatory domain" generally refers herein to a range from several kb to several tens of kb upstream of said chromosomal gene. A transcriptional regulatory domain can be identified, for example, by a method comprising (1) determining the 5' terminal by a common method such as a 5'-RACE method (e.g., can be performed by using 5'-full Race Core Kit (Takara Bio) or the like), oligo-capping method, or Si primer mapping, and (ii) using Genome Walker Kit (Clontech) or the like to obtain a 5'-upstream region to measure promotor activity of the obtained upstream region.

A nucleic acid encoding a reporter protein (hereinafter, referred to as a "reporter gene") is linked downstream of a transcriptional regulatory domain of an LRG gene in a functionable form to construct a reporter protein expression vector. Such a vector may be prepared by a method known to those skilled in the art. That is, a transcriptional regulatory domain of an LRG gene cut out in accordance with a common genetic engineering method described in "Molecular Cloning: A Laboratory Manual 2nd edition" (1989), Cold Spring Harbor Laboratory Press, "Current Protocols In Molecular Biology" (1987), John Wiley & Sons, Inc. or the like can be incorporated onto a plasmid comprising a reporter gene.

Examples of a reporter gene include beta-glucuronidase (GUS), luciferase, chloramphenicol transacetylase (CAT), beta-galactosidase (GAS), green fluorescent protein (GFP), yellow fluorescent protein (YFP), blue fluorescent protein (CFP), red fluorescent protein (RFP) and the like.

A reporter gene made by linking a prepared transcriptional regulatory domain of an LRG gene in a functionable form can be introduced into a suitable host cell by using a common genetic engineering method to insert the reporter gene into a vector that can be used in a cell where it is introduced and making a plasmid. A stable transformed cell can be obtained by culturing in a medium with a selection condition matching a selection marker gene in a vector. Alternatively, a reporter gene made by linking a transcriptional regulatory domain of an LRG gene in a functionable form can be transiently expressed in a host cell.

Further, a method corresponding to individual reporter genes may be used as a method of measuring the amount of expression of the reporter gene. For example, when a luciferase gene is used as a reporter gene, an extract of the aforementioned transformed cell is obtained after the cell is cultured for several days, and the extract is then reacted with luciferin and ATP to produce chemiluminescence, and the emission intensity thereof is measured so that promoter activity can be detected. At this time, a commercially available luciferase reaction detection kit such as PicaGene Dual Kit (registered trademark; Toyo Ink) can be used.

Specific examples of a method of measuring the amount of protein of LRG includes (i) a method of competitively reacting the antibody for detection of the present invention with a sample solution and labeled LRG and detecting a labeled protein bound to the antibody to quantify LRG in the sample solution, and
(ii) a method of simultaneously or sequentially reacting a sample solution with the antibody for detection of the present invention insolubilized on a carrier and another labeled antibody for detection of the present invention, and measuring the amount (activity) of a labeling agent on the insolubilized carrier to quantify LRG in the sample solution, and the like.

The detection and quantification of the protein expression level of LRG can be performed in accordance with a known method such as a western blot method using an antibody that recognizes LRG. A western blot method can be performed by using an antibody that recognizes LRG as a primary antibody and using an antibody that binds to the primary antibody labeled with a radioisotope such as an enzyme such as horseradish peroxidase (HRP), fluorescent substance, $^{125}$I, or the like for labeling as a secondary antibody, and measuring a signal from these label substances with a radiation detector (BAS-1800II, Fuji Film), a fluorescence detector, or the like. Further, it is also possible to use an antibody that recognizes LRG as a primary antibody and utilize ECL Plus Western Blotting Detection System (Amersham Pharmacia Biotech) for detection in accordance with the protocol for measurement with a Multi Bio Imager STORM 860 (Amersham Pharmacia Biotech).

The above-described antibody is not particularly limited in terms of its form and may be a polyclonal antibody having LRG as an immunogen or a monoclonal antibody. Furthermore, it is also possible to use an antibody having an antigen binding property against a polypeptide generally consisting of at least 8 consecutive amino acids preferably 15 consecutive amino acids, and more preferably 20 consecutive amino acids in an amino acid sequence constituting LRG.

A manufacturing method of such antibodies is already well known. The antibodies of the present invention can also be manufactured in accordance with such conventional methods (Current protocols in Molecular Biology edit. Ausubel et al. (1987) Publish. John Wiley and Sons. Section 11.12-11.13).

It is desirable in the above-described quantification method of (ii) that two types of antibodies recognize different parts of LRG. For example, if one of the antibodies is an antibody recognizing the N-terminal moiety of LRG, it is possible to use an antibody that reacts with the C-terminal moiety of the protein as the other antibody.

For example, radioisotopes, enzymes, fluorescent substances, luminescent substances and the like are used as a labelling agent used in a measurement method using a labelling substance. For example $[^{125}I]$, $[^{131}I]$, $[^{3}H]$, $[^{14}C]$ or the like is used as a radioisotope. As the above-described enzyme, an enzyme with stability and large specific activity is preferred. For example, beta-galactosidase, beta-glucosidase, alkaline phosphatase, peroxidase, malate dehydrogenase and the like are used. As a fluorescent substance, for example, fluorescamine, fluorescein isothiocyanate and the like are used. As a luminescent substance, for example, luminol, luminol derivative, luciferin, lucigenin and the like are used. Furthermore, biotin-(strept) avidins can be used to bind an antibody or antigen with a labelling agent.

A quantification method of LRG using the antibody for detection of the present invention is not particularly limited. Any method of measurement may be used as long as it is a measurement method for detecting the amount of antibody, antigen or antibody-antigen complex corresponding to the amount of antigens in a sample solution by chemical or physical means and calculating the amount with standard curves made by using a standard solution comprising a known amount of antigens. For example, nephelometry, competition method, immunometric method, and sandwich method are optimally used. For example, the sandwich method discussed below is preferably used from the viewpoint of sensitivity and specificity.

For insolubilization of an antigen or antibody, physical adsorption may be used, or a chemical bond that is generally used in insolubilization/fixation of a protein, enzyme or the like may be used. Examples of a carrier include insoluble polysaccharides such as agarose, dextran, and cellulose, synthetic resins such as silicone, polyacrylamide, polystyrene, glass and the like.

In a sandwich method, LRG in a sample solution can be quantified by reacting the sample solution with the insolubilized antibody for detection of the present invention (primary reaction) and reacting another labeled antibody for detection of the present invention (secondary reaction) and then measuring the amount or activity of a labeling agent on an insolubilized carrier. The primary reaction and the secondary reaction can be performed in the reverse order, simultaneously, or at staggered times. A labeling agent and a method of insolubilization can be in accordance with those discussed above. Further, antibodies used for a solid-phased antibody or labeled antibody is not necessarily one type of antibody in an immunoassay method by a sandwich method. A mixture of two or more types of antibodies may be used in order to improve measurement sensitivity of the like.

The antibody for detection of the present invention can be used in measurement systems other than a sandwich method, such as competition method, immunometric method, or nephelometry.

A competitive method quantifies LRG in a sample solution by competitively reacting LRG in a sample solution and labeled LRG to an antibody, separating unreacted labeled antigen (F) and labeled antigen (B) bound to an antibody (B/F separation), and measuring the amount of labels in either B or F. The reaction method uses a liquid phase method for performing B/F separation by using a soluble antibody as the antibody and using a secondary antibody to said antibody (primary antibody) or polyethylene glycol, and a solid phase method either using a solid phase antibody as a primary antibody (direct method) or using a soluble primary antibody and using a solid phase antibody as a secondary antibody (indirect method).

In an immunometric method, LRG in a sample solution and solid phase LRG are competitively reacted to a certain amount of labeled antibody and then the solid phase and liquid phase are separated, or LRG in a sample solution and an excessive amount of labeled antibody are reacted which is then added to solid phase LRG to have unreacted labeled antibody bind to a solid phase and then the solid phase and liquid phase are separated. The amount of labels in either phase is measured to quantify the amount of antigen in the sample solution.

Nephelometry measures the amount of insoluble precipitate generated as a result of an antigen-antibody reaction in a gel or solution. In cases where the amount of LRG in a sample solution is minute such that only a small amount of precipitate can be obtained, laser nephelometry or the like that utilizes scattered laser can be optimally used.

It is not necessary to set any special condition, operation or the like in applying each of the immunological measuring methods to the quantification method of the present invention. LRG measurement system may be constructed while adding common technical consideration of those skilled in the art to the common conditions or operation method in each method. General reviews, books or the like can be referred for details on such common technical means.

For example, the following can be referred: Ed. by Hiroshi IRIE "Radioimmunoassay" (Kodansha, published in 1974); Ed. by Hiroshi IRIE "Zoku Radioimmunoassay" [Sequel Radioimmunoassay] (Kodansha, published in 1979); Ed. by Eiji ISHIKAWA et al., "Koso Meneki Sokuteiho" [Enzyme immunoassay] (Igaku Shoin, published in 1978); Ed. by Eiji ISHIKAWA et al., "Koso Meneki Sokuteiho" [Enzyme immunoassay] (Second Edition) (Igaku Shoin, published in 1982); Ed. by Eiji ISHIKAWA et al., "Koso Meneki Sokuteiho" [Enzyme immunoassay] (Third Edition) (Igaku Shoin, published in 1987); "Methods in ENZYMOLOGY" Vol. 70 (Immunochemical Techniques (Part A)); Vol. 73 (Immunochemical Techniques (Part B)) of the same; Vol. 74 (Immunochemical Techniques (Part C)) of the same; Vol. 84 (Immunochemical Techniques (Part D: Selected Immunoassays)) of the same; Vol. 92 (Immunochemical Techniques (Part E: Monoclonal Antibodies and General Immunoassay Methods)) of the same; Vol. 121 (Immunochemical Techniques (Part I: Hybridoma Technology and Monoclonal Antibodies)) of the same (all published by Academic Press), and the like.

As described above, the amount of LRG in a cell can be quantified with excellent sensitivity by using the antibody for detection of the present invention.

For example, when the amount of LRG expression (amount of mRNA or protein) in the presence of a test substance is inhibited by about 20% or more, preferably about 30% or more, and more preferably about 50% or more in comparison to the amount in the absence of the test substance in the above-described screening method, such a test substance can be selected as a substance inhibiting the expression of LRG, thus as a candidate anti-inflammatory substance.

Alternatively, it is possible to use a cell comprising a reporter gene under control of a transcriptional regulatory domain endogenous to an LRG gene instead of a cell expressing the LRG gene in the above-described screening method. Such a cell may be an individual transgenic animal or a cell, tissue, or organ thereof introduced with a reporter gene (e.g., luciferase, GFP or the like) under control of a transcriptional regulatory domain of an LRG gene. When such a cell is used, the amount of LRG expression can be assessed by measuring the expression level of a reporter gene by using a conventional method.

(Measurement of Function of LRG)

The screening method of the present invention can be performed by using whether a test substance inhibits the function of LRG as an indicator.

LRG is mainly a protein secreted from neutrophils to blood. It is understood that a substance having the ability to bind to an LRG protein can inhibit the function of LRG by blocking the interaction between the LRG protein and a protein which is a binding partner thereof (e.g., LRG receptor on a target cell surface). Thus, candidate substances for inhibiting the function of LRG can be screened, with the binding ability to LRG as an indicator.

For example, it is possible to detect a test substance having the ability to bind to LRG by having the test substance adsorb to each well of a well plate, adding an LRG solution labeled with a suitable labeling agent to each well, incubating the solution, removing a liquid phase, and measuring the amount of label bound to a solid phase after washing. Instead of directly labeling LRG, it is possible to detect LRG bound to a solid phase by using a labeled anti-LRG antibody. Alternatively, a solution of a test substance is passed through a carrier with solidified LRG (e.g., affinity column), and the test substance retained by the carrier can be selected as a substance having the ability to bind to LRG, i.e., as a candidate anti-inflammatory substance.

It is possible to verify whether a candidate substance obtained as such in fact has anti-inflammatory action by applying the candidate substance to an inflammation model and testing whether an inflammatory reaction is suppressed in the model. As such an inflammation model, in vivo and in vitro models can be used. For example, IBD models such as DSS induced colitis model (which can be prepared by having a nonhuman animal drink water containing 3-5% (w/v) DSS with a molecular weight of 5000-10000 for 5-10 days) and TNBS induced colitis model (which can be prepared by rectally administering TNBS dissolved in 50% ethanol in a nonhuman animal at the amount of for example 50 µg/g weight), RA models such as CIA model (which can be prepared by immunizing a nonhuman animal with a complete Freund's adjuvant and an emulsified type II collagen) or CAIA model (which can be prepared by injecting into a nonhuman animal a monoclonal antibody cocktail recognizing an epitope in CB11 of type II collagen) or the like can be used as an in vivo model, which is not limited thereto. Meanwhile, in vitro models include, but are not limited to, culture systems (e.g., Caco-2 cell culture system, culture system of synovial fibroblasts derived from synovial tissue of an RA patient and the like) of a target cell in an inflammatory disease (e.g., intestinal epithelial cell in IBD, synovial cells in RA or the like) and the like. Such in vitro models can elicit an inflammatory reaction by a stimulation from an inflammatory cytokine such as TNF alpha, reactive oxygen such as $H_2O_2$, LPS, or the like, composite culture with an inflammatory cytokine producing cell such as a monocyte, macrophage, or neutrophil (e.g., culture system using a Transwell™ culture system having each of monocultures of target cells (e.g., Caco-2 cells) in the upper compartment and inflammatory cytokine producing cells (macrophage-like THP-1 cells, RAW 264.7 cells) in the bottom compartment) or the like as needed.

It is possible to determine whether a candidate substance has anti-inflammatory action from whether an inflammatory reaction in the above-described inflammation model is suppressed by the addition of the candidate substance. For example, for the above-described drug induced colitis model animal, the presence and/or the level of anti-inflammatory effect can be determined by using change in weight (suppression of weight loss due to onset of colitis, extent of recovery from weight loss, or the like), shortening of the length of large intestine, injury on the epithelium at the site of intestinal inflammation, extent of inflammatory cell infiltration, or the like as an indicator. Meanwhile, when a monolayer culturing system of intestinal epithelial cells, which is an in vitro inflammatory bowel disease model, is used, the level of inflammatory reaction can be assessed by using decrease in a transepithelial electrical resistance (TER) value, LDH production, or increase in IL-8 expression as an indicator.

In another preferred embodiment of the present invention, a substance inhibiting the function of LRG can be screened by testing the activity to inhibit binding of an LRG protein to a binding protein thereof (e.g., LRG receptor). An LRG receptor or a biological substance binding to LRG has not been identified. However, since LRG is mainly a protein secreted from neutrophils into blood, the presence of a physiological binding partner of LRG in a protein expressed on a surface of a target cell in an inflammatory disease is strongly suggested. Thus, a test substance can be selected as a candidate for an anti-inflammatory substance when a fraction of a membrane of the target cell (e.g., fraction of a membrane on a lamina propria side in case of intestinal epithelial cells) is isolate in accordance with a conventional method and a solid phase is formed on a suitable carrier and a labeled LRG proteins is contacted with the solid phase in the presence and absence of the test substance, the amount of LRG bound to the fraction of the cell membrane in the presence of the test substance is significantly lower in comparison to the amount of LRG bound to the fraction of the cell membrane in the absence of the test substance. It is possible to verify whether a candidate substance selected in this manner has anti-inflammatory action by a method similar to those described above.

In still another embodiment of the present invention, substances exhibiting anti-inflammatory action by inhibiting the function of LRG can be screened in a single process by using the above-described in vitro inflammation model. The method comprises the following steps (1)-(3).

(1) contacting a target cell of an inflammatory disease with a test substance in the presence and absence of LRG,
(2) measuring the level of an inflammatory reaction in the cell under each condition, and
(3) selecting a test substance that suppresses an inflammatory reaction in the presence of LRG, but not in the absence of LRG in comparison to a measurement in the absence of the test substance as a candidate of a substance exhibiting anti-inflammatory action by inhibiting the function of LRG.

Such a method may further comprise eliciting an inflammation before or after the above-described (1) or simultaneously therewith as needed. Examples of a method of eliciting an inflammation include a stimulation from an inflammatory cytokine such as TNF alpha, reactive oxygen such as $H_2O_2$, LPS or the like, composite culture with an inflammatory cytokine producing cell such as a monocyte, macrophage, or neutrophil and the like. An example of a preferred embodiment includes a method using a Transwell™ culture system having each of monocultures of target cells (e.g., Caco-2 cells) in the upper compartment and inflammatory cytokine producing cell (macrophage-like THP-1 cells, RAW 264.7 cells) in the lower compartment. In this case, LRG is added to a medium in the lower compartment. LPS or the like may further be added to the medium to elicit an inflammation. A test substance is generally added to the medium in the lower compartment. However, a test substance may be added to the medium in the upper compartment when, for example, the intention is to screen components contained in food which can be absorbed in the intestine and inhibit the function of LRG or an LRG function inhibitor that can be administered orally or the like.

A substance for inhibiting the expression or function of LRG obtained by one of the above-described screening methods of the present invention is useful as a prophylactic and/or therapeutic pharmaceutical for an inflammatory disease.

A compound obtained by using the screening method of the present invention, when used as the aforementioned prophylactic/therapeutic agent, can be formulated in a similar manner to the above-described lower molecular weight compound that inhibits the expression or function of LRG. Such a compound can be administered orally or parenterally to a human or mammal (e.g., mouse, rat, rabbit, sheep, pig, cow, horse, cat, dog, monkey, chimpanzee or the like) through the same route of administration and dosage.

The following Examples are merely for specific illustration of the present invention and are not intended to limit the scope of the present invention.

EXAMPLES

Reference Example 1

Production of LRG Deletion Mice

LRG homozygous deletion mice were produced by the following method.

A mouse LRG gene (Lrg1) was obtained PCR and inserted into a vector having a diphtheria toxin sequence.

The following modification was added to make a targeting vector. A neomycin-resistant gene (Neo) sandwiched by FRT sequences was inserted downstream of a coding region of an Lrg1 gene (exon 2), and Loxp sequences were each inserted upstream of exon 2 and downstream of Neo. The targeting vector was introduced into a mouse ES cell by electroporation, and a neomycin-resistant ES clone was selected. Homologous recombinant clones were identified by PCR for use in the production of a chimeric mouse. Offsprings of the chimeric mouse were screened by PCR to obtain a heterozygous mouse of interest. By crossbreeding with FLP expressing transgenic mice and Cre expressing transgenic mice, each of Neo and Lrg sequences were deleted in order. Lrg homozygous deletion mice were obtained from the mating of the resulting Lrg1 heterozygous deletion mice.

Reference Example 2

Increase in Blood LRG Concentration in DDS Inducing Colitis Model

Wild-type mice (C57BL/6 mice) (sex: male; age: 8 weeks; 5 mice) were allowed to drink water containing 3% dextran sulfate sodium (DSS) for 5 days. Thereafter, the mice were raised with normal water. After 7 days from the start of supplying DSS, blood was collected from two wild-type mice. When the blood LRG concentration was measured by ELISA, increase in blood LRG concentration was observed in the DSS treated group relative to the control group (no DSS treatment group) (FIG. 1).

Example 3

Effect of LRG Deletion on DSS Induced Colitis

Figure 2:
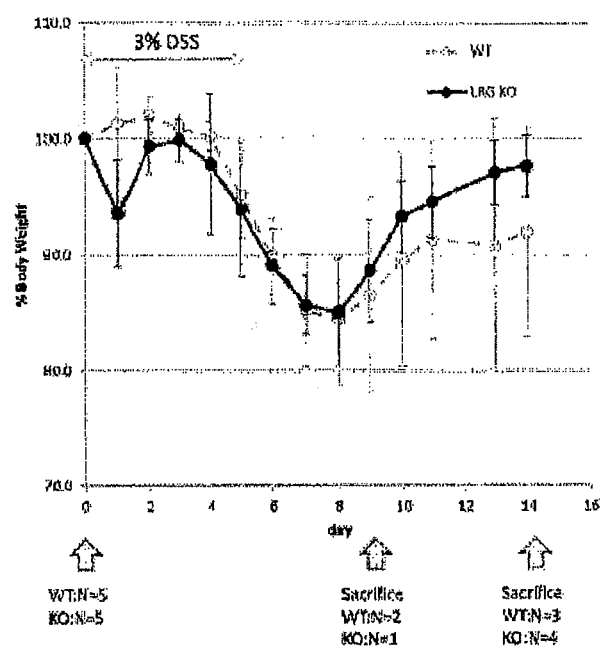
FIG. 2 is a diagram showing a change in body weight of wild type mice (WT) and LRG knockout mice (LRG KO) in which colitis is induced with DSS. Colitis was induced by allowing the intake of 3% DSS for 5 days (N=5). On day 9, two WT and 1 KO were subjected to another experiment (hereinafter, WT: N=3, KO: N=4).

The body weight of DSS induced colitis model mice produced by the same method as Reference Example 2 (5 of each of LRG deletion mice and wild-type mice were used) was measured every other day until 14 days after the start of supplying DSS (4 LRG deletion mice and 3 wild type mice on and after day 10). As a result, similar level of weight loss was observed between the LRG deletion mice group and wild-type mice group. However, for the recovery in body weight thereafter, it was found that the body weight returned thereafter to normal earlier in the LRG deletion mouse group (FIG. 2).

Figure 3A:
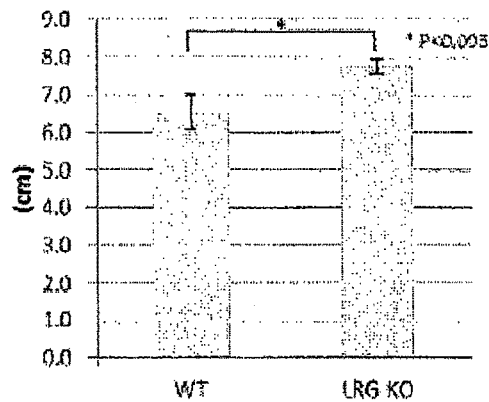
In FIG. 3A, "*" indicates that the p value for WT is less than 0.005 (by t-test).
Figure 3B:
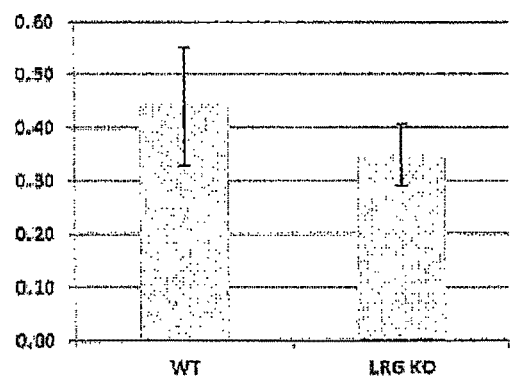
FIG. 3 is a diagram showing the colon length (A) and colon weight/length ratios (B) in wild type mice (WT) and LRG knockout mice (LRG KO) in which colitis is induced with DSS. Due to the progression of colitis, the colon is truncated and the weight per a length of the colon (weight/length ratio) increases from edema or cellular infiltration associated with an inflammation.

Next, mice were slaughtered after 14 days from the start of supplying DSS to measure the body weight and length and weight of the large intestine. As a result, the large intestine was shortened by supplying DSS in wild-type mice, while shortening in the length of the large intestine was not observed in LRG deletion mice (p<0.005; FIG. 3A). Further, the weight/length ratio of the large intestine had a tendency to decrease in LRG deletion mice relative to wild-type mice (FIG. 3B). Significance test was carried out by t-test.

Reference Example 4

Production of Rheumatoid Arthritis Model 5 mg of anti-type II collagen antibody cocktail (Chondrex, arthritis eliciting monoclonal antibody cocktail (5-clone)) was peritoneally administered to the LRG deletion mice produced in Reference Example 1 and corresponding wild-type mice (C57BL/6 mice) (sex: female; age: 6 weeks; 2 mice each). Furthermore, 50 μg of LPS was peritoneally administered after 3 days and 13 days.

Example 5

Effect of LRG Deletion on Rheumatoid Arthritis

Figure 4:
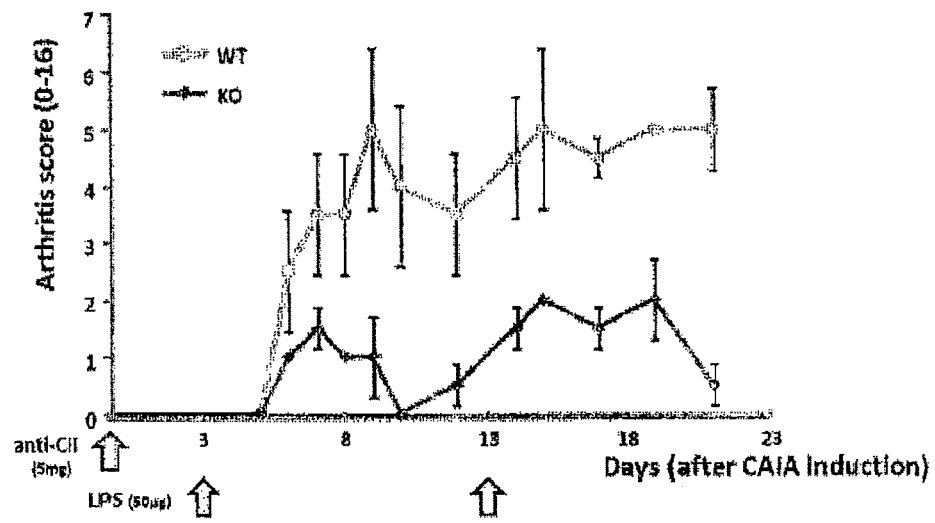
FIG. 4 is a diagram showing arthritis scores in wide type mice (WT) and LRG knockout mice (KO) in which arthritis (CAIA) is induced by administering an anti-type II collagen antibody cocktail (Chondrex). 5 mg/mouse of an antibody cocktail was peritoneally administered and LPS was peritoneally administered at 50 µg/mouse on day 3 and day 13 to observe arthritic symptoms (arthritis score 0-16).

Arthritis scores were measured from the start of arthritis induction to after 14 days for 2 of each of LRG deletion mice and wild-type mice. As a result, arthritis scores were lower for the LRG deletion mouse group than in the wild-type mouse group (FIG. 4). Arthritis scores were evaluated by a standard method (J Immunol Methods. 2009 Mar. 31; 343 (1): 49-55).

The above results indicate that LRG contributes to exacerbation of the pathological conditions of ulcerative colitis and rheumatoid arthritis.

INDUSTRIAL APPLICABILITY

The present invention provides a prophylactic and/or therapeutic agent for an inflammatory disease targeting LRG, which is a different factor from conventional targets of a therapeutic agent. A therapeutic drug with a new working mechanism is provided, so that better therapy can be provided to inflammatory disease patient for whom an effect of recovery from a pathological condition is not observed or insufficient with existing therapeutic methods and inflammatory disease patients who have acquired resistance to an existing therapeutic drug by continuous use of the drug. Furthermore, the present invention can be used for prophylactic purposes to prevent an inflammatory disease in advance and for purposes to prevent recurrence of a disease in a patient who has at one time experienced remission of an inflammatory disease. Further, according to the present invention, it is possible to screen candidate substances for a novel prophylactic/therapeutic drug for an inflammatory disease, which exerts anti-inflammatory action by inhibiting the expression or function of LRG.

The present application is based on Japanese Patent Application No. 2013-083397 filed in Japan (filing date: Apr. 11, 2013). The present specification encompasses the entire content thereof.

The invention claimed is:

1. A method for preventing and/or treating an inflammatory disease in a subject, comprising administering to the subject an effective amount of a substance for inhibiting expression or function of a leucine rich alpha 2 glycoprotein (LRG).

2. The method of claim 1, wherein the substance for inhibiting the expression of LRG is
   (a) an antisense nucleic acid to a transcription product of an LRG gene,
   (b) a ribozyme nucleic acid to a transcription product of an LRG gene, or
   (c) a nucleic acid having RNAi activity against a transcription product of an LRG gene or a precursor thereof.

3. The method of claim 1, wherein the substance for inhibiting the function of LRG is an antibody against LRG.

4. The method of claim 1, wherein the inflammatory disease is an inflammatory bowel disease or an inflammatory autoimmune disease.

5. The method of claim 4, wherein the inflammatory bowel disease or the inflammatory autoimmune disease is ulcerative colitis or rheumatoid arthritis.

* * * * *

SEQUENCE LISTING

<160> NUMBER OF SEQ ID NOS: 4

<210> SEQ ID NO 1
<211> LENGTH: 1780
<212> TYPE: DNA
<213> ORGANISM: Homo sapiens

<400> SEQUENCE: 1

```
gcagagctac catgtcctct tggagcagac agcgaccaaa aagcccaggg ggcattcaac      60
cccatgtttc tagaactctg ttcctgctgc tgctgttggc agcctcagcc tgggggtca      120 ccctgagccc caaagactgc aggtgttccg ctcagacca tggcagctcc atctcctgtc      180
aaccacctgc cgaaatcccc ggctacctgc agccgacac cgtgcacctg gccgtggaat      240
tcttcaacct gacccacctg ccagccaacc tcctccaggg cgcctctaag ctccaagaat      300
tgcacctctc cagcaatggg ctggaaagcc tctcgcccga attcctgcgg ccagtgccgc      360
agctgagggt gctggatcta acccgaaacg ccctgaccgg gctgccccg ggcctcttcc      420 aggcctcagc caccctggac accctggtat tgaaagaaaa ccagctggag gtcctggagg      480
tctcgtggct acacggcctg aaagctctgg ggcatctgga cctgtctggg aaccgcctcc      540
ggaaactgcc cccgggctg ctggccaact tcaccctcct gcgcacccct tgaccttgggg      600 agaaccagtt ggagaccttg ccacctgacc tcctgagggg tccgctgcaa ttagaacggc      660
tacatctaga aggcaacaaa ttgcaagtac tgggaaaaga tctcctcttg ccgcagccgg      720
acctgcgcta cctcttcctg aacggcaaca agctggccag ggtggcagcc ggtgccttcc      780
agggcctgcg gcagctggac atgctggacc tctccaataa ctcactggcc agcgtgcccg      840
aggggctctg gcatcccta gggcagccaa actgggacat gcgggatggc ttcgacatct      900
ccggcaaccc ctggatctgt gaccagaacc tgagcgacct ctatcgttgg cttcaggccc      960
aaaaagacaa gatgttttcc cagaatgaca cgcgctgtgc tgggcctgaa gccgtgaagg     1020
gccagacgct cctggcagtg gccaagtccc agtgagacca ggggcttggg ttgagggtgg     1080
ggggtctggt agaacactgc aacccgctta acaaataatc ctgcctttgg ccgggtgcgg     1140
gggctcacgc ctgtaatccc agcactttgg gaggcccagg tgggcggatc acgaggtcag     1200
gagatcgaga ccatcttggc taacatggtg aaaccctgtc tctactaaaa atataaaaaa     1260
ttagccaggc gtggtggtgg gcacctgtag tcccagcaac tcgggaggct gaggcaggag     1320
aatggcgtga acttgggagg cggagcttgc ggtgagccaa gatcgtgcca ctgcactcta     1380
gcctgggcga cagagcaaga ctgtctcaaa aaaattaaaa ttaaaattaa aaacaaataa     1440
tcctgccttt tacaggtgaa actcggggct gtccatagcg gctgggaccc cgtttcatcc     1500
atccatgctt cctagaacac acgatgggct ttccttaccc atgcccaagg tgtgccctcc     1560
gtctggaatg ccgttccctg tttcccagat ctcttgaact ctgggttctc ccagccccctt     1620 gtccttcctt ccagctgagc cctggccaca ctggggctgc cttctctgat ctctgtcttc     1680
cccaagtcag ggggctctct gagtgcaggg tctgatgctg agtcccactt agcttggggt     1740
cagaaccaag gggtttaata aataaccctt gaaaactgga                          1780
```

<210> SEQ ID NO 2
<211> LENGTH: 347
<212> TYPE: PRT
<213> ORGANISM: Homo sapiens

<400> SEQUENCE: 2

```
Met Ser Ser Trp Ser Arg Gln Arg Pro Lys Ser Pro Gly Gly Ile Gln
1               5                   10                  15

Pro His Val Ser Arg Thr Leu Phe Leu Leu Leu Leu Ala Ala Ser
            20                  25                  30

Ala Trp Gly Val Thr Leu Ser Pro Lys Asp Cys Gln Val Phe Arg Ser
        35                  40                  45

Asp His Gly Ser Ser Ile Ser Cys Gln Pro Pro Ala Glu Ile Pro Gly
    50                  55                  60
```

```
Tyr Leu Pro Ala Asp Thr Val His Leu Ala Val Glu Phe Phe Asn Leu
 65                  70                  75                  80

Thr His Leu Pro Ala Asn Leu Leu Gln Gly Ala Ser Lys Leu Gln Glu
                 85                  90                  95

Leu His Leu Ser Ser Asn Gly Leu Glu Ser Leu Ser Pro Glu Phe Leu
            100                 105                 110

Arg Pro Val Pro Gln Leu Arg Val Leu Asp Leu Thr Arg Asn Ala Leu
        115                 120                 125

Thr Gly Leu Pro Pro Gly Leu Phe Gln Ala Ser Ala Thr Leu Asp Thr
    130                 135                 140

Leu Val Leu Lys Glu Asn Gln Leu Glu Val Leu Glu Val Ser Trp Leu
145                 150                 155                 160

His Gly Leu Lys Ala Leu Gly His Leu Asp Leu Ser Gly Asn Arg Leu
                165                 170                 175

Arg Lys Leu Pro Pro Gly Leu Leu Ala Asn Phe Thr Leu Leu Arg Thr
            180                 185                 190

Leu Asp Leu Gly Glu Asn Gln Leu Glu Thr Leu Pro Pro Asp Leu Leu
        195                 200                 205

Arg Gly Pro Leu Gln Leu Glu Arg Leu His Leu Glu Gly Asn Lys Leu
    210                 215                 220

Gln Val Leu Gly Lys Asp Leu Leu Leu Pro Gln Pro Asp Leu Arg Tyr
225                 230                 235                 240

Leu Phe Leu Asn Gly Asn Lys Leu Ala Arg Val Ala Ala Gly Ala Phe
                245                 250                 255

Gln Gly Leu Arg Gln Leu Asp Met Leu Asp Leu Ser Asn Asn Ser Leu
            260                 265                 270

Ala Ser Val Pro Glu Gly Leu Trp Ala Ser Leu Gly Gln Pro Asn Trp
        275                 280                 285

Asp Met Arg Asp Gly Phe Asp Ile Ser Gly Asn Pro Trp Ile Cys Asp
    290                 295                 300

Gln Asn Leu Ser Asp Leu Tyr Arg Trp Leu Gln Ala Gln Lys Asp Lys
305                 310                 315                 320

Met Phe Ser Gln Asn Asp Thr Arg Cys Ala Gly Pro Glu Ala Val Lys
                325                 330                 335

Gly Gln Thr Leu Leu Ala Val Ala Lys Ser Gln
            340                 345

<210> SEQ ID NO 3
<211> LENGTH: 1372
<212> TYPE: DNA
<213> ORGANISM: Mus musculus

<400> SEQUENCE: 3 ggtgggact  atataaagcc  accttcctgg  ggtcttgagg  acagacatag  aggagcagct    60
atggtctctt  ggcagcatca  aggaagcctc  caggatctca  agacctgcct  tgccagaacc   120
ctgtttctcc  tggcccctctt  gggcagggtg  tccagcctca  aggaatgcct  gatactgcag   180
tcggctgagg  gtagcaccgt  ctcctgccat  ggtcccaccg  agtttccgag  ctccctccct   240
gccgacactg  tccatctgtc  ggtggaattc  ccaacctga  cgcagctgcc  cgccgccgcc   300
ctgcaagggt  gtccgggtct  gcgggagctg  cacctctcga  gcaatcgcct  gcaggcgctg   360
tctcccgagt  tgctggcgcc  cgtgcccgg  ctgcgcgccc  tggatctgac  ccgcaatgct   420
ctccgcagcc  tgccccccgg  gttgttcagc  acctcggcca  acctgagcac  cctggtcctg   480
```

```
agggagaacc agctgcggga ggtgagcgcg caatggcttc agggcctgga cgccctgggc      540
cacttggacc tggcggagaa ccagctgagt tcgctgccct ccgggctcct cgccagcctc      600
ggcgccctgc acaccctcga ccttgggtac aacctgctgg agtcgctgcc cgagggactc      660
ctgcggggcc caaggcggct gcagcgcctg cacctggaag ggaaccgact gcagaggctg      720
gaggatagcc tgcttgcgcc ccaaccgttc ctgcgcgtcc tgttcctgaa tgacaaccag      780
ttggtcgggg tggcgaccgg ctccttccag ggcctacagc acctggatat gttggatctg      840
tccaataact ctctgtccag cacgccccg ggcctgtggg cgttcctggg gaggccgacc      900
cgcgacatgc aggacggctt cgacatctcc acaaccccct ggatctgtga caagaacctg      960
gcggaccttt gccgctggct ggtcgccaac cgaaacaaga tgttctcaca gaacgacacg     1020
cgctgtgcgg ggccccgaggc catgaagggt cagcggctgc tggacgtggc agagctgggg     1080
tccctgtgag gatgatggct ggggtgctgg ccaagggcac cccgctcgcc actgagccaa     1140
tgtggtccca tgtcagtgtg cagattcctc attccctcag ccaggaatgc tattctcgga     1200
ctccctctct gggtcctctc cactcgccac aactcttcca cctctcactc ttcctgtgcc     1260 ggccccagg ccaccttgtg tttatctggc tttgacacgt ctgtttcagg ggtcaccaaa     1320
gcagttaata aaacggctcc taggctgact gaaaaaaaaa aaaaaaaaaa aa             1372
```

<210> SEQ ID NO 4
<211> LENGTH: 342
<212> TYPE: PRT
<213> ORGANISM: Mus musculus

<400> SEQUENCE: 4

```
Met Val Ser Trp Gln His Gln Gly Ser Leu Gln Asp Leu Lys Thr Cys
1               5                   10                  15

Leu Ala Arg Thr Leu Phe Leu Leu Ala Leu Leu Gly Arg Val Ser Ser
            20                  25                  30

Leu Lys Glu Cys Leu Ile Leu Gln Ser Ala Glu Gly Ser Thr Val Ser
        35                  40                  45

Cys His Gly Pro Thr Glu Phe Pro Ser Ser Leu Pro Ala Asp Thr Val
    50                  55                  60

His Leu Ser Val Glu Phe Ser Asn Leu Thr Gln Leu Pro Ala Ala Ala
65                  70                  75                  80

Leu Gln Gly Cys Pro Gly Leu Arg Glu Leu His Leu Ser Ser Asn Arg
                85                  90                  95

Leu Gln Ala Leu Ser Pro Glu Leu Leu Ala Pro Val Pro Arg Leu Arg
            100                 105                 110

Ala Leu Asp Leu Thr Arg Asn Ala Leu Arg Ser Leu Pro Pro Gly Leu
        115                 120                 125

Phe Ser Thr Ser Ala Asn Leu Ser Thr Leu Val Leu Arg Glu Asn Gln
    130                 135                 140

Leu Arg Glu Val Ser Ala Gln Trp Leu Gln Gly Leu Asp Ala Leu Gly
145                 150                 155                 160

His Leu Asp Leu Ala Glu Asn Gln Leu Ser Ser Leu Pro Ser Gly Leu
                165                 170                 175

Leu Ala Ser Leu Gly Ala Leu Thr Leu Asp Leu Gly Tyr Asn Leu
            180                 185                 190

Leu Glu Ser Leu Pro Glu Gly Leu Leu Arg Gly Pro Arg Arg Leu Gln
        195                 200                 205

Arg Leu His Leu Glu Gly Asn Arg Leu Gln Arg Leu Glu Asp Ser Leu
    210                 215                 220
```

-continued

```
Leu Ala Pro Gln Pro Phe Leu Arg Val Leu Phe Leu Asn Asp Asn Gln
225                 230                 235                 240

Leu Val Gly Val Ala Thr Gly Ser Phe Gln Gly Leu Gln His Leu Asp
                245                 250                 255

Met Leu Asp Leu Ser Asn Asn Ser Leu Ser Ser Thr Pro Pro Gly Leu
            260                 265                 270

Trp Ala Phe Leu Gly Arg Pro Thr Arg Asp Met Gln Asp Gly Phe Asp
        275                 280                 285

Ile Ser His Asn Pro Trp Ile Cys Asp Lys Asn Leu Ala Asp Leu Cys
        290                 295                 300

Arg Trp Leu Val Ala Asn Arg Asn Lys Met Phe Ser Gln Asn Asp Thr
305                 310                 315                 320

Arg Cys Ala Gly Pro Glu Ala Met Lys Gly Gln Arg Leu Leu Asp Val
                325                 330                 335

Ala Glu Leu Gly Ser Leu
                340
```